(12) United States Patent
Shelton, IV et al.

(10) Patent No.: US 12,171,428 B2
(45) Date of Patent: Dec. 24, 2024

(54) FIRING MEMBER TRACKING FEATURE FOR SURGICAL STAPLER

(71) Applicant: Cilag GmbH International, Zug (CH)

(72) Inventors: Frederick E. Shelton, IV, Hillsboro, OH (US); Kevin M. Fiebig, Cincinnati, OH (US); Shane R. Adams, Lebanon, OH (US); Nicholas J. Ross, Franklin, OH (US); Matthew D. Cowperthwait, Cincinnati, OH (US); Curtis A. Maples, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 568 days.

(21) Appl. No.: 17/402,738

(22) Filed: Aug. 16, 2021

(65) Prior Publication Data

US 2023/0049736 A1    Feb. 16, 2023

(51) Int. Cl.
| | |
|---|---|
| *A61B 17/072* | (2006.01) |
| *A61B 17/00* | (2006.01) |
| *A61B 90/00* | (2016.01) |

(52) U.S. Cl.
CPC ...... *A61B 17/072* (2013.01); *A61B 17/00234* (2013.01); *A61B 2017/00057* (2013.01); *A61B 2017/00115* (2013.01); *A61B 2017/07271* (2013.01); *A61B 2017/07285* (2013.01); *A61B 2090/0811* (2016.02)

(58) Field of Classification Search
CPC ............ A61B 17/072; A61B 17/07207; A61B 17/00234; A61B 17/285; A61B 2017/07271; A61B 2017/07278; A61B 2017/07285; A61B 2017/00057; A61B 2017/00075; A61B 2017/00115; A61B 2017/00128; A61B 2017/295; A61B 2090/0811
See application file for complete search history.

(56) References Cited

U.S. PATENT DOCUMENTS

| | | |
|---|---|---|
| 5,129,570 A | 7/1992 | Schulze et al. |
| 7,404,508 B2 | 7/2008 | Smith et al. |

(Continued)

FOREIGN PATENT DOCUMENTS

| | | |
|---|---|---|
| EP | 2789299 A1 | 10/2014 |
| EP | 2839786 A1 | 2/2015 |

(Continued)

OTHER PUBLICATIONS

International Search Report and Written Opinion dated Nov. 28, 2022 for Application No. PCT/IB2022/057604, 15 pgs.

(Continued)

*Primary Examiner* — Stephen F. Gerrity
*Assistant Examiner* — Linda J Hodge
(74) *Attorney, Agent, or Firm* — Frost Brown Todd LLP

(57) ABSTRACT

An apparatus includes a shaft assembly, an end effector, and a drive member visualization assembly. The end effector includes a first jaw, a second jaw, a staple cartridge, and a drive member capable of actuating along a firing stroke to fire a plurality of staples out of the staple cartridge or to sever tissue. The drive member visualization assembly provides an electronic indication linked to a physical location of the drive member within the upper jaw and the lower jaw during the firing stroke.

17 Claims, 28 Drawing Sheets

(56) References Cited

U.S. PATENT DOCUMENTS

| | | | |
|---|---|---|---|
| 7,434,715 B2 | 10/2008 | Shelton, IV et al. | |
| 7,721,930 B2 | 5/2010 | McKenna et al. | |
| 7,810,692 B2* | 10/2010 | Hall | A61B 17/07207 227/176.1 |
| 7,832,408 B2 | 11/2010 | Shelton, IV et al. | |
| 7,845,537 B2 | 12/2010 | Shelton, IV et al. | |
| 8,083,120 B2 | 12/2011 | Shelton, IV et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,708,213 B2 | 4/2014 | Shelton, IV et al. | |
| 9,060,770 B2 | 6/2015 | Shelton, IV et al. | |
| 9,186,142 B2 | 11/2015 | Fanelli et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,487 B2 | 12/2017 | Dachs, II | |
| 10,011,018 B2 | 7/2018 | McGrogan et al. | |
| 10,092,292 B2 | 10/2018 | Boudreaux et al. | |
| 10,307,170 B2 | 6/2019 | Parfett et al. | |
| 10,485,621 B2 | 11/2019 | Morrissette et al. | |
| 10,537,400 B2 | 1/2020 | Dachs, II et al. | |
| 10,610,313 B2 | 4/2020 | Bailey et al. | |
| 10,667,809 B2 | 6/2020 | Bakos et al. | |
| 10,806,530 B2 | 10/2020 | Liao et al. | |
| 10,863,988 B2 | 12/2020 | Patel et al. | |
| 11,020,138 B2 | 6/2021 | Ragosta | |
| 11,026,755 B2 | 6/2021 | Weir et al. | |
| 11,076,926 B2 | 8/2021 | Ragosta et al. | |
| 11,147,552 B2 | 10/2021 | Burbank et al. | |
| 11,166,773 B2 | 11/2021 | Ragosta et al. | |
| 11,234,700 B2 | 2/2022 | Ragosta et al. | |
| 11,259,884 B2 | 3/2022 | Burbank | |
| 2006/0185682 A1 | 8/2006 | Marczyk | |
| 2009/0114701 A1 | 5/2009 | Zemlok et al. | |
| 2010/0069942 A1* | 3/2010 | Shelton, IV | A61B 17/07207 227/175.1 |
| 2011/0036891 A1* | 2/2011 | Zemlok | A61B 17/07207 227/176.1 |
| 2012/0116267 A1* | 5/2012 | Kimball | G16H 20/40 606/1 |
| 2012/0209288 A1* | 8/2012 | Robinson | A61B 34/20 606/130 |
| 2012/0209314 A1 | 8/2012 | Weir et al. | |
| 2015/0297228 A1 | 10/2015 | Huitema et al. | |
| 2016/0361126 A1 | 12/2016 | Schena et al. | |
| 2017/0020617 A1 | 1/2017 | Weir et al. | |
| 2017/0105732 A1* | 4/2017 | Scheib | A61B 17/068 |
| 2017/0265865 A1 | 9/2017 | Burbank | |
| 2017/0265954 A1 | 9/2017 | Burbank et al. | |
| 2017/0333037 A1 | 11/2017 | Wellman et al. | |
| 2018/0146962 A1* | 5/2018 | Kostrzewski | A61B 17/07207 |
| 2018/0168756 A1 | 6/2018 | Liao et al. | |
| 2018/0271608 A1 | 9/2018 | Ragosta et al. | |
| 2018/0310935 A1 | 11/2018 | Wixey | |
| 2018/0325606 A1 | 11/2018 | Weir et al. | |
| 2018/0344419 A1 | 12/2018 | Dachs, II et al. | |
| 2019/0038371 A1 | 2/2019 | Wixey et al. | |
| 2019/0076142 A1 | 3/2019 | Wixey | |
| 2019/0076143 A1 | 3/2019 | Smith | |
| 2019/0167266 A1 | 6/2019 | Patel et al. | |
| 2019/0200989 A1 | 7/2019 | Burbank et al. | |
| 2019/0239967 A1 | 8/2019 | Ragosta et al. | |
| 2019/0262088 A1 | 8/2019 | Burbank | |
| 2020/0138529 A1 | 5/2020 | Ragosta et al. | |
| 2020/0397430 A1 | 12/2020 | Patel et al. | |
| 2020/0405301 A1 | 12/2020 | Shelton, IV et al. | |
| 2021/0393340 A1 | 12/2021 | Beckman et al. | |
| 2021/0401433 A1 | 12/2021 | Freidel et al. | |

FOREIGN PATENT DOCUMENTS

| | | |
|---|---|---|
| EP | 2992839 A2 | 3/2016 |
| EP | 3155983 A1 | 4/2017 |
| WO | WO 2015/153642 A1 | 10/2015 |
| WO | WO 2017/083125 A1 | 5/2017 |
| WO | WO 2017/083129 A1 | 5/2017 |
| WO | WO 2018/049198 A1 | 3/2018 |
| WO | WO 2018/049206 A1 | 3/2018 |
| WO | WO 2018/049211 A1 | 3/2018 |
| WO | WO 2018/049217 A1 | 3/2018 |
| WO | WO 2018/052806 A1 | 3/2018 |
| WO | WO 2018/052810 A1 | 3/2018 |
| WO | WO 2018/071497 A1 | 4/2018 |
| WO | WO 2018/071763 A1 | 4/2018 |
| WO | WO 2018/085529 A2 | 5/2018 |
| WO | WO 2018/175467 A1 | 9/2018 |
| WO | WO 2019/165403 A1 | 8/2019 |
| WO | WO 2020/131290 A1 | 6/2020 |

OTHER PUBLICATIONS

U.S. Appl. No. 17/402,674, entitled "Surgical Stapler End Effector Sled Having Cartridge Wall Support Feature," filed Nov. 4, 2020.
U.S. Appl. No. 17/402,674, entitled "Methods of Operating a Robotic Surgical Stapler," filed Aug. 16, 2021.
U.S. Appl. No. 17/402,675, entitled "Multi-Threshold Motor Control Algorithm for Powered Surgical Stapler," filed Aug. 16, 2021.
U.S. Appl. No. 17/402,677, entitled "Variable Response Motor Control Algorithm for Powered Surgical Stapler," filed Aug. 16, 2021.
U.S. Appl. No. 17/402,695, entitled "Powered Surgical Stapler Having Independently Operable Closure and Firing Systems," filed Aug. 16, 2021.
U.S. Appl. No. 17/402,695, entitled "Firing System Features for Surgical Stapler," filed Aug. 16, 2021.
U.S. Appl. No. 17/402,701, entitled "Multiple-Sensor Firing Lockout Mechanism for Powered Surgical Stapler," filed Aug. 16, 2021.
U.S. Appl. No. 17/402,703, entitled "Proximally Located Firing Lockout Mechanism for Surgical Stapler," filed Aug. 16, 2021.
U.S. Appl. No. 17/402,720, entitled "Cartridge-Based Firing Lockout Mechanism for Surgical Stapler," filed Aug. 16, 2021.
U.S. Appl. No. 17/402,732, entitled "Multi-Position Restraining Member for Sled Movement," filed Aug. 16, 2021.
U.S. Appl. No. 17/402,744, entitled "Adjustable Power Transmission Mechanism for Powered Surgical Stapler," filed Aug. 16, 2021.
U.S. Appl. No. 17/402,749, entitled "Firing Bailout System for Powered Surgical Stapler," filed Aug. 16, 2021.
U.S. Appl. No. 17/402,759, entitled "Deflectable Firing Member for Surgical Stapler," filed Aug. 16, 2021.

* cited by examiner

FIRING MEMBER TRACKING FEATURE FOR SURGICAL STAPLER

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. Patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
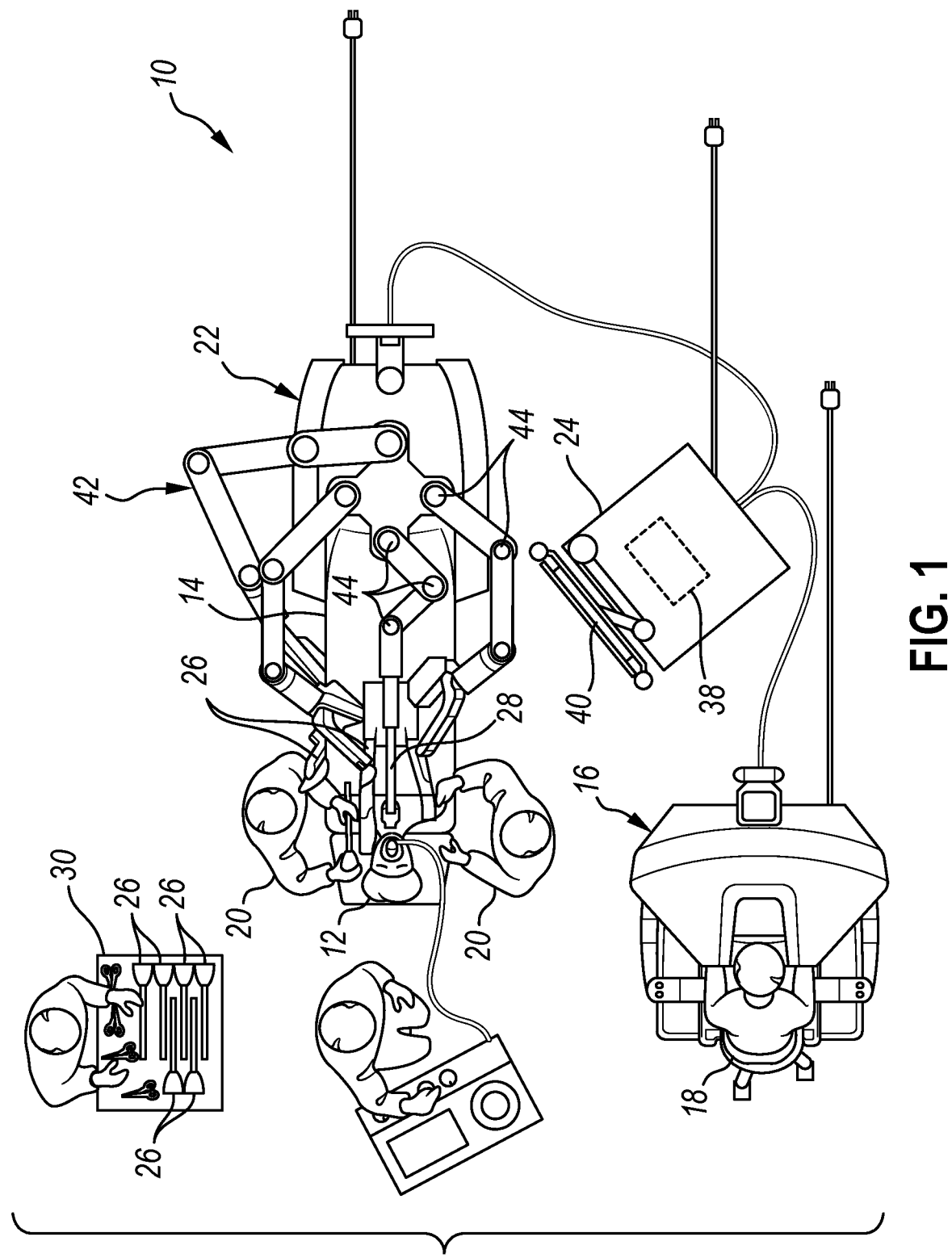
FIG. 1 depicts a top plan view of a robotic surgical system being used to perform a surgical procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "inner," "outer," "upper," "lower," and the like also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

I. Exemplary Robotic Surgical System

A. Overview

FIG. 1 shows a top plan view of an exemplary robotic surgical system (10) that may be used for performing a diagnostic or surgical procedure on a patient (12) who is lying down on an operating table (14). Robotic surgical system (10) may be constructed and operable in accordance with at least some of the teachings of U.S. Pat. No. 9,839,487, entitled "Backup Latch Release for Surgical Instrument," issued Dec. 12, 2017; U.S. Pat. No. 10,485,621, entitled "Sterile Barrier Between Surgical Instrument and Teleoperated Actuator," issued Nov. 26, 2019; U.S. Pat. No. 10,806,530, entitled "System and Method for Patient-Side Instrument Control," issued Oct. 20, 2020; U.S. Pat. No. 10,537,400, entitled "Detection Pins to Determine Presence of Surgical Instrument and Adapter on Manipulator," issued Jan. 21, 2020; U.S. Pat. No. 10,863,988, entitled "Surgical Instrument with Lockout Mechanism," published Dec. 15, 2020; U.S. Pat. No. 10,610,313, entitled "Surgical Instrument with Shiftable Transmission," issued Apr. 7, 2020; U.S. Pub. No. 2018/0271608, entitled "Manual Release for Medical Device Drive System," published Sep. 27, 2018; U.S. Pub. No. 2018/0325606, entitled "Systems and Methods for Operating an End Effector," published Nov. 15, 2018; U.S. Pub. No. 2019/0200989, entitled "Stapler Reload Detection and Identification," published Jul. 4, 2019; U.S. Pub. No. 2019/0239967, entitled "Stapler Beam Architecture," published Aug. 8, 2019; U.S. Pub. No. 2019/0262088, entitled "Robotic Surgical Stapler Assembly Configured to Use Stapler Reload," published Aug. 29, 2019; U.S. Pub. No. 2019/0239877, entitled "Wrist Architecture," published Aug. 8, 2019; U.S. Pub. No. 2019/0201150, entitled "Push-Pull Surgical Instrument End Effector Actuation Using Flexible Tension Member," published Jul. 4, 2019; U.S. Pub. No. 2019/0282233, entitled "Stapler Cartridge With an Integral Knife," published Sep. 19, 2019; U.S. Pub. No. 2019/0262088, entitled "Robotic Surgical Stapler Assembly Configured to Use Stapler Reload," published Aug. 29, 2019; U.S. Pub. No. 2020/0138529, entitled "Locking System for Medical Device Drive System," published May 7, 2020; and/or U.S. Pub. No. 2020/0397430, entitled "Surgical Instrument With Lockout Mechanism," published Dec. 24, 2020. The disclosure of each of the above-cited U.S. Patents and U.S. Patent Publications is incorporated by reference herein in its entirety.

Robotic surgical system (10) may include a surgeon's console (16) for use by a surgeon (18) during a surgical procedure. One or more assistants (20) may also participate in the procedure. Robotic surgical system (10) may include a patient side cart (22) (i.e., a surgical robot) and an electronics cart (24). Patient side cart (22) may manipulate at least one surgical instrument (26) (also referred to as a "tool assembly" or "tool") through an incision in the body of patient (12) while surgeon (18) views the surgical site through surgeon's console (16). As will be described in greater detail below, surgical instrument(s) (26) and an imaging device (shown as an endoscope (28)) may be removably coupled with patient side cart (22). Electronics cart (24) may be used to process the images of the surgical site for subsequent display to the surgeon (18) through surgeon's console (16). Electronics cart (24) may be coupled with endoscope (28) and may include a processor (38) (shown schematically) to process captured images for subsequent display, such as to surgeon (18) on the surgeon's console (16), on a display (40) of electronics cart (24), or another suitable display located locally and/or remotely. The images may also be processed by a combination of electronics cart (24) and processor (38), which may be coupled together to process the captured images jointly, sequentially, and/or combinations thereof. Electronics cart (24) may overlay the captured images with a virtual control interface prior to displaying combined images to the surgeon (18) via surgeon's console (16).

Figure 2:
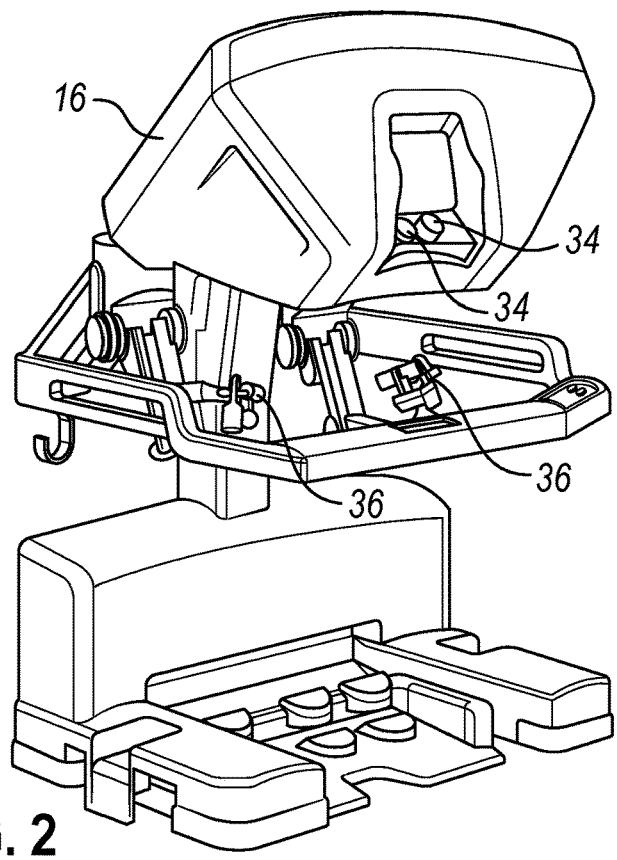
FIG. 2 depicts a perspective view of a surgeon's control console of the robotic surgical system of FIG. 1.

FIG. 2 shows a perspective view of surgeon's console (16). Surgeon's console (16) includes a left eye display (32) and a right eye display (34) for presenting surgeon (18) with a coordinated stereo view of the surgical site that enables depth perception. Surgeon's console (16) includes one or more input control devices (36) causing patient side cart (22) (shown in FIG. 1) to manipulate one or more surgical instruments (26). Input control devices (36) may provide the same degrees of freedom as their associated surgical instruments (26) (shown in FIG. 1) to provide surgeon (18) with telepresence, or the perception that the input control devices (36) are integral with surgical instruments (26). To this end, position, force, and tactile feedback sensors (not shown) may be employed to transmit position, force, and tactile sensations from surgical instruments (26) back to the surgeon's hands through input control devices (36). In some instances, surgeon's console (16) may be located in the same room as the patient so that surgeon (18) may directly monitor the procedure, be physically present if necessary, and speak to an assistant directly rather than over the telephone or other communication medium. Alternatively, surgeon (18) may be located in a different room, a completely different building, or other remote location from the patient allowing for remote surgical procedures.

Figure 3:
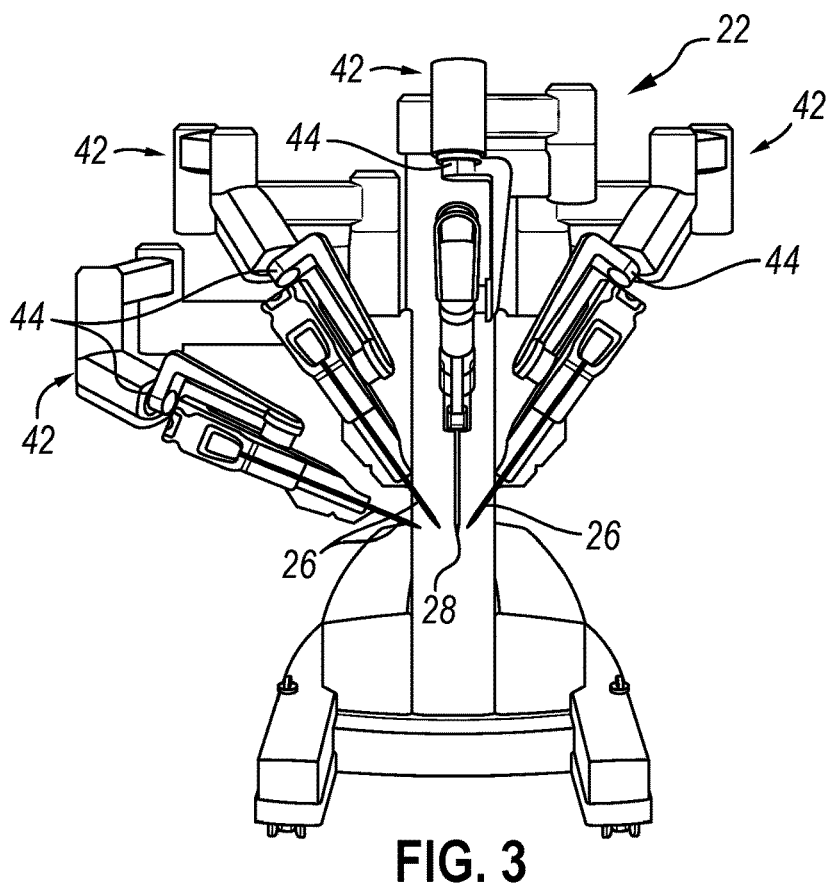
FIG. 3 depicts a front elevation view of a patient side cart of the robotic surgical system of FIG. 1.

FIG. 3 shows patient side cart (22) that manipulates surgical instruments (26). An image of the surgical site may be obtained by endoscope (28), which may include a stereoscopic endoscope. Manipulation is provided by robotic mechanisms, shown as robotic arms (42) that include at least one robotic joint (44) and an output coupler (not shown) that is configured to removable secure surgical instrument (26) with robotic arm (42). Endoscope (28) and surgical tools (26) may be positioned and manipulated through incisions in the patient so that a kinematic remote center is maintained at the incision to minimize the size of the incision. Images of the surgical site may include images of the distal ends of the surgical instruments (26) when they are positioned within the field-of-view of the endoscope (28). Patient side cart (22) may output the captured images for processing outside electronics cart (24). The number of surgical instruments (26) used at one time will generally depend on the diagnostic or surgical procedure and the space constraints within the operating room, among other factors. To change one or more of surgical instruments (26) being used during a procedure, assistant(s) (20) may remove surgical instrument (26) from patient side cart (22) and replace surgical instrument (26) with another surgical instrument (26) from a tray (30) (shown in FIG. 1) in the operating room.

B. Exemplary Surgical Instrument

Figure 4:
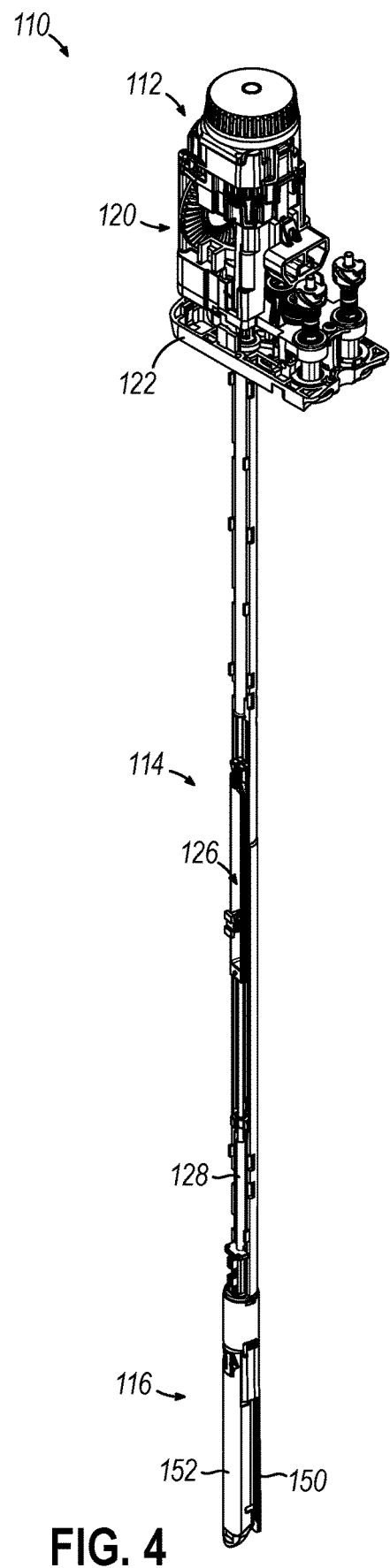
FIG. 4 depicts a perspective view of an exemplary surgical instrument that may be used with the robotic surgical system of FIG. 1, where the surgical instrument includes an instrument base, an elongate shaft, and an end effector, with select portions of the surgical instrument omitted to reveal internal features.
Figure 5:
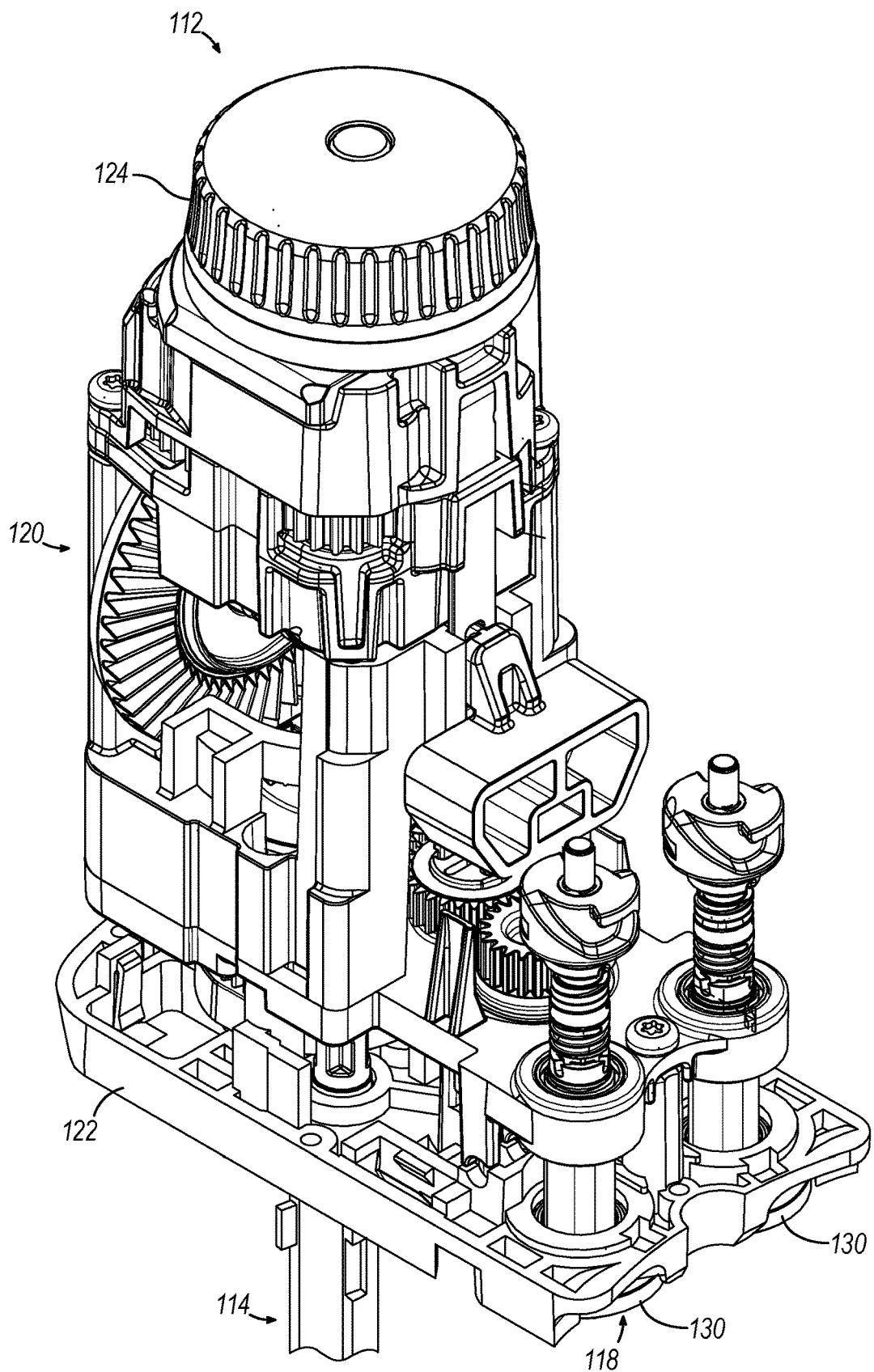
FIG. 5 depicts an enlarged perspective view of the instrument base of the surgical instrument of FIG. 4, with an outer housing omitted to reveal internal features.

FIGS. 4-5 show an exemplary surgical instrument (110) that may be mounted on and used with patient side cart (22) shown in FIG. 3. Surgical instrument (110) can have any of a variety of configurations capable of performing one or more surgical functions. As shown, surgical instrument (110) includes an instrument base (112), a shaft assembly (114) extending distally from instrument base (112), and an end effector (116) at a distal end of shaft assembly (114). Instrument base (112) includes an attachment interface (118) that includes input couplers (130) that are configured to interface with and be driven by corresponding output couplers (not shown) of robotic arm (42) of patient side cart (22).

FIG. 5 shows an enlarged perspective view of instrument base (112) of surgical instrument (110). Instrument base (112) includes a drive system (120) mounted on a chassis (122) and having one or more actuators for actuating end effector (116) to clamp, staple, and cut tissue, and for articulating end effector (116) relative to a longitudinal axis defined by shaft assembly (114). Drive system (120) may include a manual actuator (124), which is shown in the form of a knob configured to be manually rotated. Manual actuator (124) may engage other components of surgical instrument (110) to serve as a "bailout" mechanism to obtain a desired movement in end effector (116) without powered actuation of drive system (120). Shaft assembly (114) may include additional drive components, such as portions of a drive train (126), that may couple instrument base (112) to a moveable feature (128) of shaft assembly (114) that may be coupled to end effector (116). Shaft assembly (114) may be configured for use with a variety of interchangeable end effectors (116), such as a cutter, grasper, a cautery tool, a camera, a light, or a surgical stapler, for example.

C. First Exemplary End Effector

Figure 6:
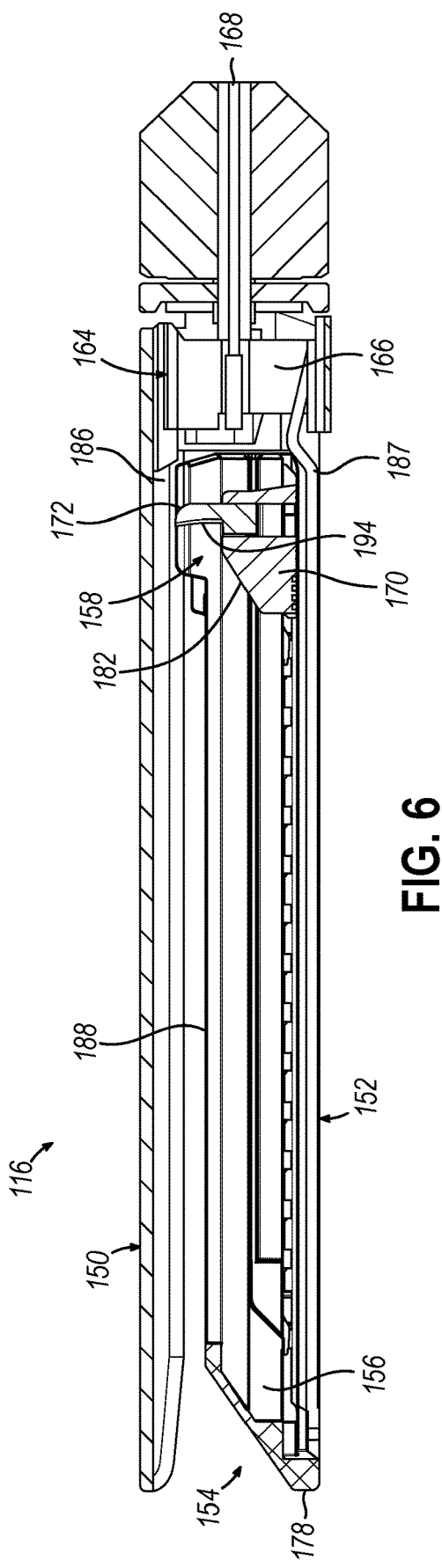
FIG. 6 depicts a side cross-sectional view of the end effector of FIG. 4, where the end effector includes a staple cartridge.

FIG. 6 shows a cross-sectional side view of end effector (116) of surgical instrument (110). End effector (116) extends distally from a distal end of shaft assembly (114). In the present example, end effector (116) comprises a surgical stapler, which may also be referred to herein as an "endocutter," configured to clamp, cut, and staple tissue. As illustrated, end effector (116) includes opposing upper and lower jaws (150, 152) configured to move relative to one another between open and closed positions for clamping and releasing tissue.

One or both of upper and lower jaws (150, 152) may be configured to pivot and thereby actuate end effector (116) between open and closed positions. Lower jaw (152) includes a removable staple cartridge (154). In the illustrated example, lower jaw (152) is pivotable relative to upper jaw (150) to move between an open, unclamped position and a closed, clamped position. In other examples, upper jaw (150) may move relative to lower jaw (152) (e.g., similar to end effector (210) of FIGS. 9-10). In still other examples, both and upper and lower jaws (150, 152) may move to actuate end effector (116) between open and closed positions. In the present example, lower jaw (152) is referred to as a "cartridge jaw" or "channel jaw," and upper jaw (150) is referred to as an "anvil jaw."

Figure 8:
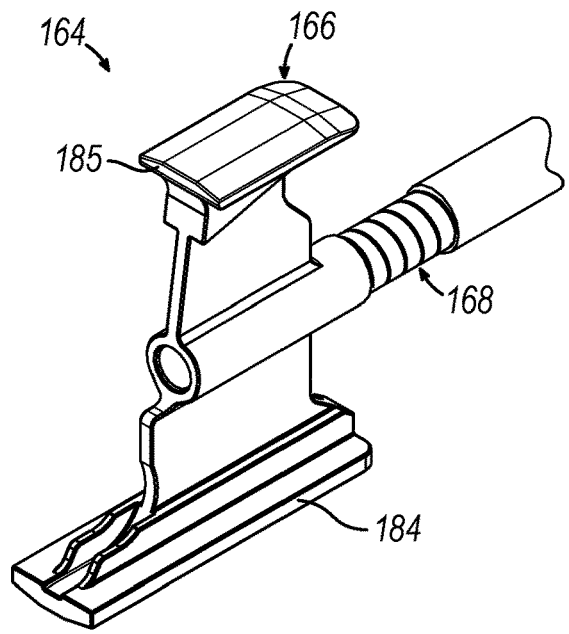
FIG. 8 depicts a driving assembly configured for use with the staple cartridge of FIG. 7.
Figure 9:
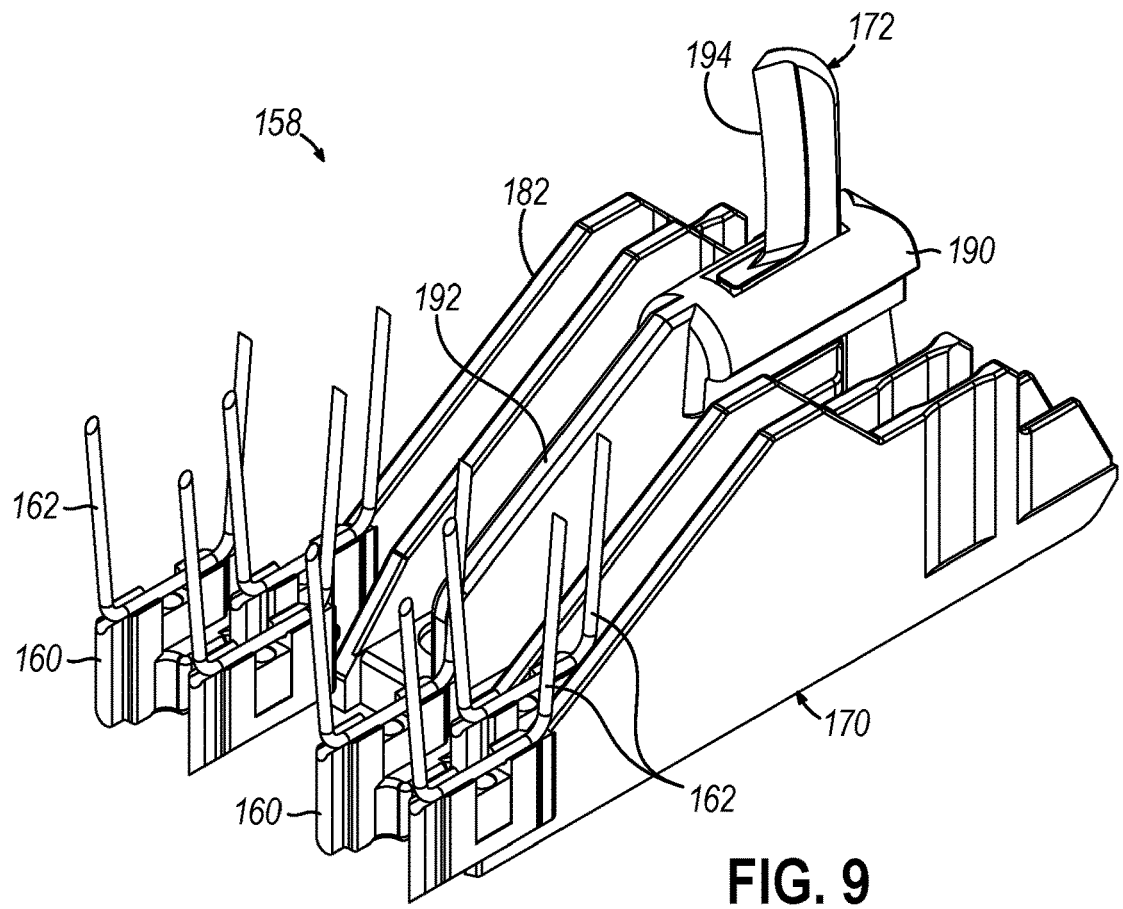
FIG. 9 depicts a firing assembly, staple drivers, and staples configured for use with the staple cartridge of FIG. 7.

Upper jaw (150) defines a surface that has a plurality of pockets (not shown) and operates as an anvil to deform staples ejected from staple cartridge (154) during operation. Staple cartridge (154) is replaceable, for example, by removing a used staple cartridge (154) from end effector (116) and inserting a new staple cartridge (154) into lower jaw (152). Staple cartridge (154) includes a staple cartridge body (156) that houses a firing assembly (158), a plurality of staple drivers (160) (also referred to as staple pushers), and a plurality of staples (162). As shown in FIGS. 6 and 8, end effector (116) includes a driving assembly (164) that includes a pusher member (166) that is operatively coupled with an actuation mechanism via a push rod (168). As shown in FIG. 6 and FIG. 9, firing assembly (158) includes a wedge sled (170) (also referred to as a staple pushing shuttle), and a knife member (172).

Figure 7:
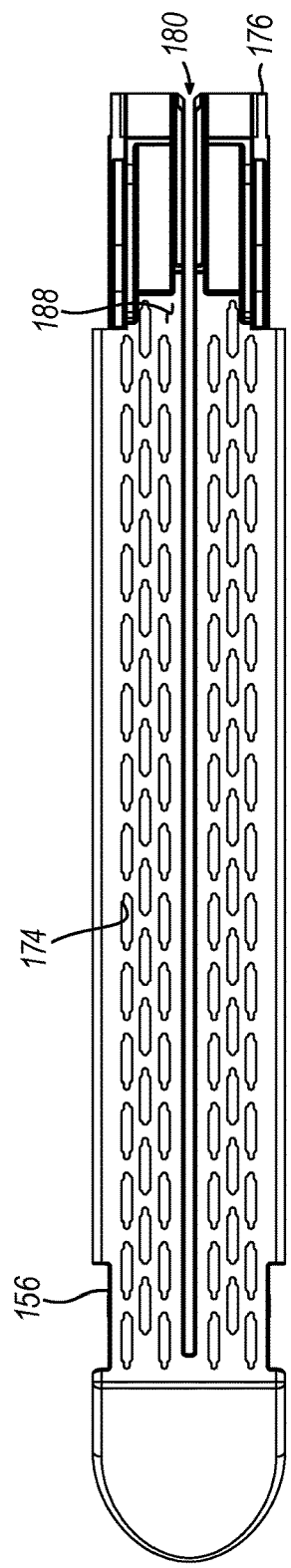
FIG. 7 depicts a top view of a deck of the staple cartridge of FIG. 6.

FIG. 7 shows a top view of staple cartridge body (156). Staple cartridge body (156) includes an array of staple accommodating apertures (174) (also known as "openings") extending through an upper deck (188) of staple cartridge body (156). Each aperture (174) slidably houses a respective staple (162) in an unformed state and a free end of a corresponding staple driver (160) positioned beneath the unformed staple (162). Staple cartridge (154) includes proximal and distal ends (176, 178). In operation, staples (162) are sequentially deployed from apertures (174) by staple drivers (160) starting at proximal end (176) and advancing toward distal end (178). A vertical slot (180), configured to accommodate knife member (172), extends through part of staple cartridge (154).

FIG. 8 shows pusher member (166) as including first and second flanges (184, 185). First flange (184) is configured to be received in a longitudinal slot (186) (shown in FIG. 6) of upper jaw (150) and second flange (185) is configured to be received in a longitudinal slot (187) (shown in FIG. 6) of staple cartridge body (156) of lower jaw (152). First and second flanges (184, 185) move along longitudinal slots (186, 187) during actuation of pusher member (166). In some versions, pusher member (166) may include a single flange (e.g., omitting first flange (184)). As shown, longitudinal slot (186) is generally enclosed and longitudinal slot (187) opens to an exterior surface of lower jaw (152).

FIG. 9 shows a perspective view of firing assembly (158), which is configured to be slidably received within the proximal end of staple cartridge body (156) in a longitudinal direction prior to engaging staple drivers (160) and staples (162). Wedge sled (170) of firing assembly (158) slidingly interfaces with staple cartridge body (156). More specifically, wedge sled (170) advances distally along staple cartridge body (156) such that ramp portions (182) of wedge sled contact staple drivers (160). Staple drivers (160) push staples (162) out of apertures (174) of staple cartridge body (156) to penetrate through and staple tissue clamped between staple cartridge body (156) and upper jaw (150). An initial distal actuation of pusher member (166) may move pusher member (166) into contact with wedge sled (170), together referred to as a driver, with further actuation pushing staples (162) transversely out of staple cartridge body (156).

At an initial proximal position of wedge sled (170), knife member (172) is housed within staple cartridge body (156). The position of knife member (172) is controlled during a first portion of the movement of wedge sled (170) from proximal end (176) of staple cartridge body (156) to distal end (178) of staple cartridge (154), so that a cutting edge (194) of knife member (172) extends through vertical slot (180). Vertical slot (180) accommodates cutting edge (194) of knife member (172) as firing assembly (158) is moved toward distal end (178) of staple cartridge (154). Wedge sled (170) includes a guide member (190) that provides a bearing surface that cooperates with a similarly shaped surface of staple cartridge body (156) to guide wedge sled (170). Guide member (190) extends from a vertical rib member (192) of wedge sled (170), which forms a central portion of wedge sled (170). In some versions, knife member (172), or at least cutting edge (194), may be retracted below upper deck (188) of staple cartridge body (156) prior to firing assembly (158) reaching its distal most position adjacent to distal end (178) of staple cartridge (154).

D. Second Exemplary End Effector

Figure 10:
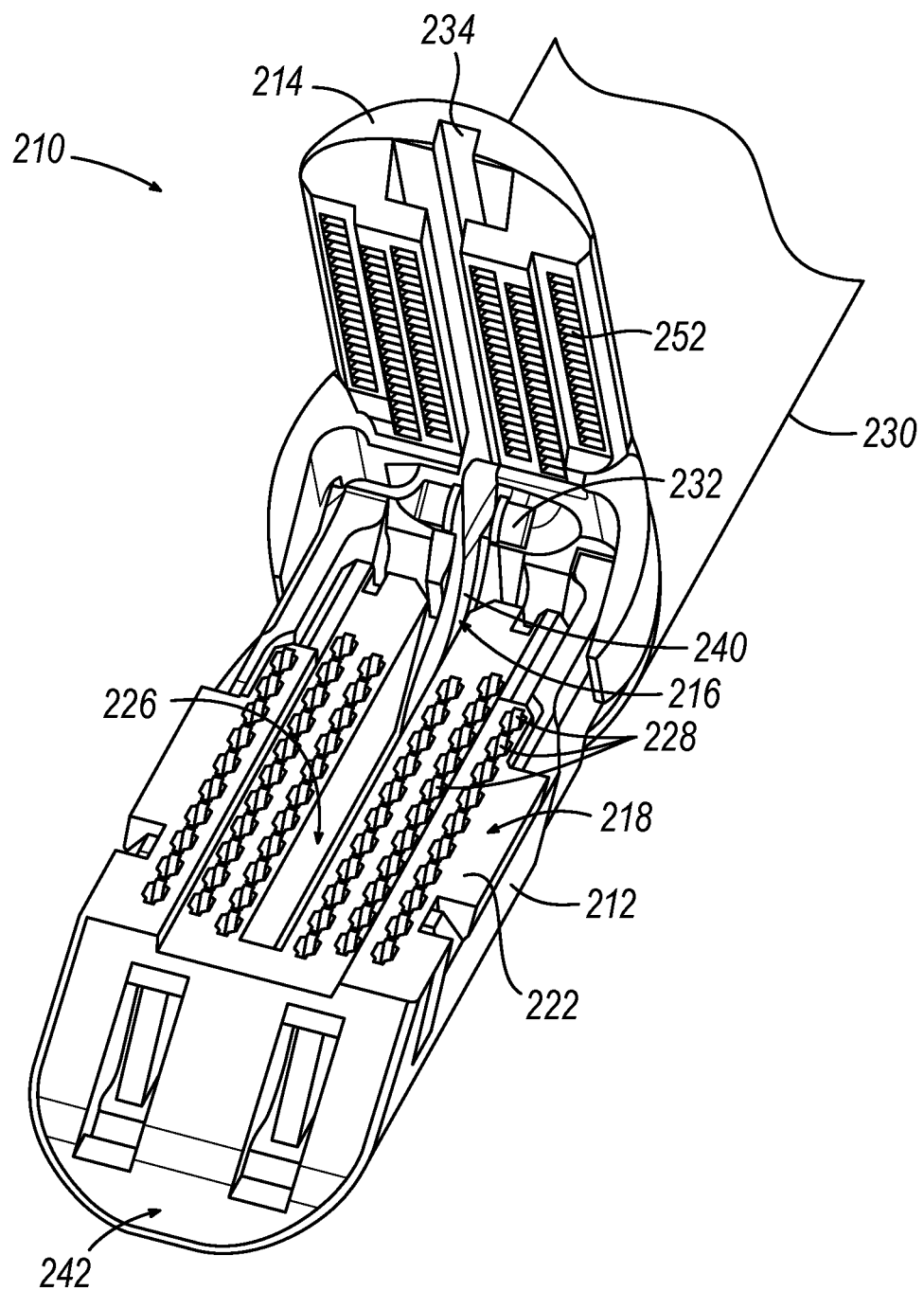
FIG. 10 depicts a second exemplary end effector that may be configured for use with the robotic surgical system of FIG. 1.
Figure 11:
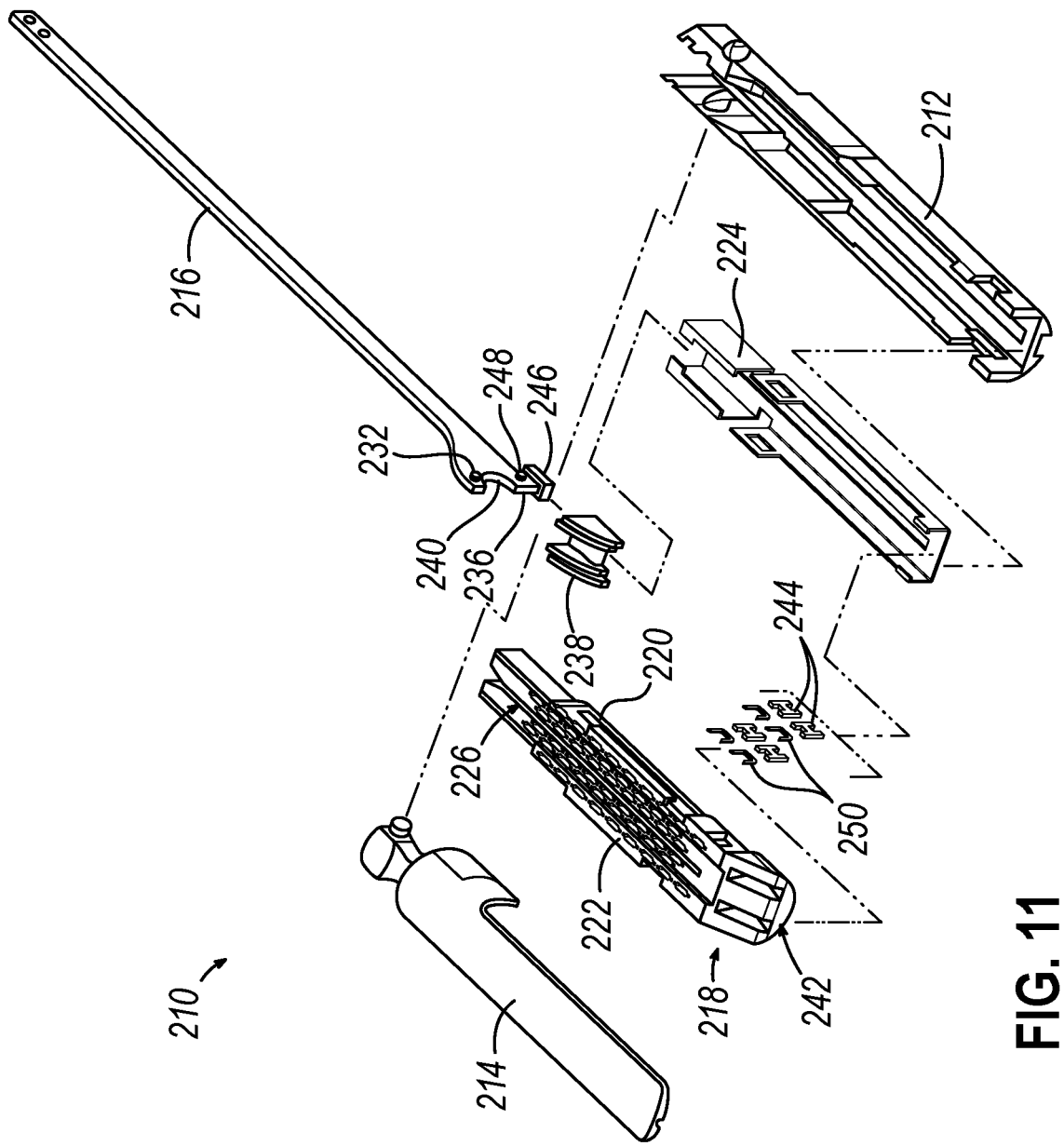
FIG. 11 depicts an exploded view of the end effector of FIG. 10.

FIGS. 10-11 show a second exemplary end effector (210), in an open position, that is configured to compress, cut, and staple tissue. End effector (210) may be configured for use with surgical instrument (110) of FIG. 4, or with surgical instruments of alternative constructions. End effector (210) may be constructed and operable in accordance with at least some of the teachings of U.S. patent application Ser. No. 16/916,295, entitled "Surgical Stapler Cartridge Retainer with Ejector Feature," filed Aug. 3, 2020, the disclosure of which is incorporated by reference herein in its entirety. End effector (210) of the present example includes a lower jaw (212) and an upper jaw in the form of a pivotable anvil (214). Lower jaw (212) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (214) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety.

FIG. 10 shows end effector (210), where anvil (214) is pivoted to an open position and a firing beam (216) is proximally positioned, allowing an unspent staple cartridge (218) to be removably installed into a channel of lower jaw (212). Staple cartridge (218) includes a cartridge body (220), which presents an upper deck (222) and is coupled with a lower cartridge tray (224). A vertical slot (226) is formed through part of staple cartridge (218) and opens upwardly through upper deck (222). One or more rows of staple apertures (228) are formed through upper deck (222) on one side of vertical slot (226), with one or more rows of staple apertures (228) being formed through upper deck (222) on the other side of vertical slot (226). End effector (210) is closed by distally advancing a closure tube (not shown) and a closure ring (230). Firing beam (216) is then advanced distally so that an upper pin of firing beam (216) enters longitudinal anvil slot (234). Simultaneously, a pusher block (236) located at the distal end of firing beam (216) engages a wedge sled (238) housed within cartridge body (220), such that wedge sled (238) is pushed distally by pusher block (236) as firing beam (216) is advanced distally through staple cartridge (218) and anvil (214).

During firing, cutting edge (240) of firing beam (216) enters vertical slot (226) toward distal end (242) of staple cartridge (218), severing tissue clamped between staple cartridge (218) and anvil (214). As best seen in FIG. 11, wedge sled (238) presents inclined cam surfaces that urge staple drivers (244) upwardly as wedge sled (238) is driven distally through staple cartridge (218). A firing beam cap (246) slidably engages a lower surface of lower jaw (212). Wedge sled (238) is movable longitudinally within staple cartridge (218), while staple drivers (244) are movable vertically within staple cartridge (218). A middle pin (248) and pusher block (236) of firing beam (216) together actuate staple cartridge (218) by entering into vertical slot (226) within staple cartridge (218), driving wedge sled (238) distally into upward camming contact with staple drivers (244) that in turn drive staples (250) out through staple apertures (228) and into forming contact with staple forming pockets (252) on the inner surface of anvil (214). Additional examples of alternative surgical instruments and/or associated features are described in U.S. patent application Ser. No. 16/946,363, entitled "Articulation Mechanisms for Robotic Surgical Tools," filed on Jun. 18, 2020, the disclosure of which is hereby incorporated by reference herein in its entirety.

It will be appreciated that any one or more of the teachings described below may be combined with any one or more of the teachings described above in connection with FIGS. 1-11.

II. Exemplary Tracking Features for Firing a Surgical Stapler

As mentioned above, pusher member (166) and wedge sled (170) of end effector (116) may be actuated distally while jaws (150, 152) grasp tissue in order to simultaneously staple and sever the grasped tissue. Similarly, pusher block (236) and wedge sled (238) of end effector (210) may be actuated distally while jaws (212, 214) grasp tissue in order to simultaneously staple and sever the grasped tissue.

In some instances, it may be desirable to visually locate, approximate, or otherwise represent the longitudinal position of pusher member (166), pusher block (236), and/or wedge sled (170, 238) within jaws (150, 152, 212, 214). For instance, a visual representation of the longitudinal position of pusher block (236) or wedge sled (170) during the firing process may inform an operator of the progress made by end effector (116, 210) in stapling and severing tissue. Further, when an image of the surgical site is obtained by endoscope (28), it may be desirable to easily view such a visual representation via endoscope (28) and display (40) without having to further manipulate the position of endoscope (28). The following show various examples that may be readily incorporated into shaft assembly (114) and/or end effector (116, 210) in order to allow an operator to visually locate, approximate and/or otherwise represent the longitudinal location of pusher member (166), pusher block (236), and/or wedge sled (170, 238) within jaws (150, 152, 212, 214).

A. End Effector with Illumination Feature Associated with Wedge Sled

Figure 12:
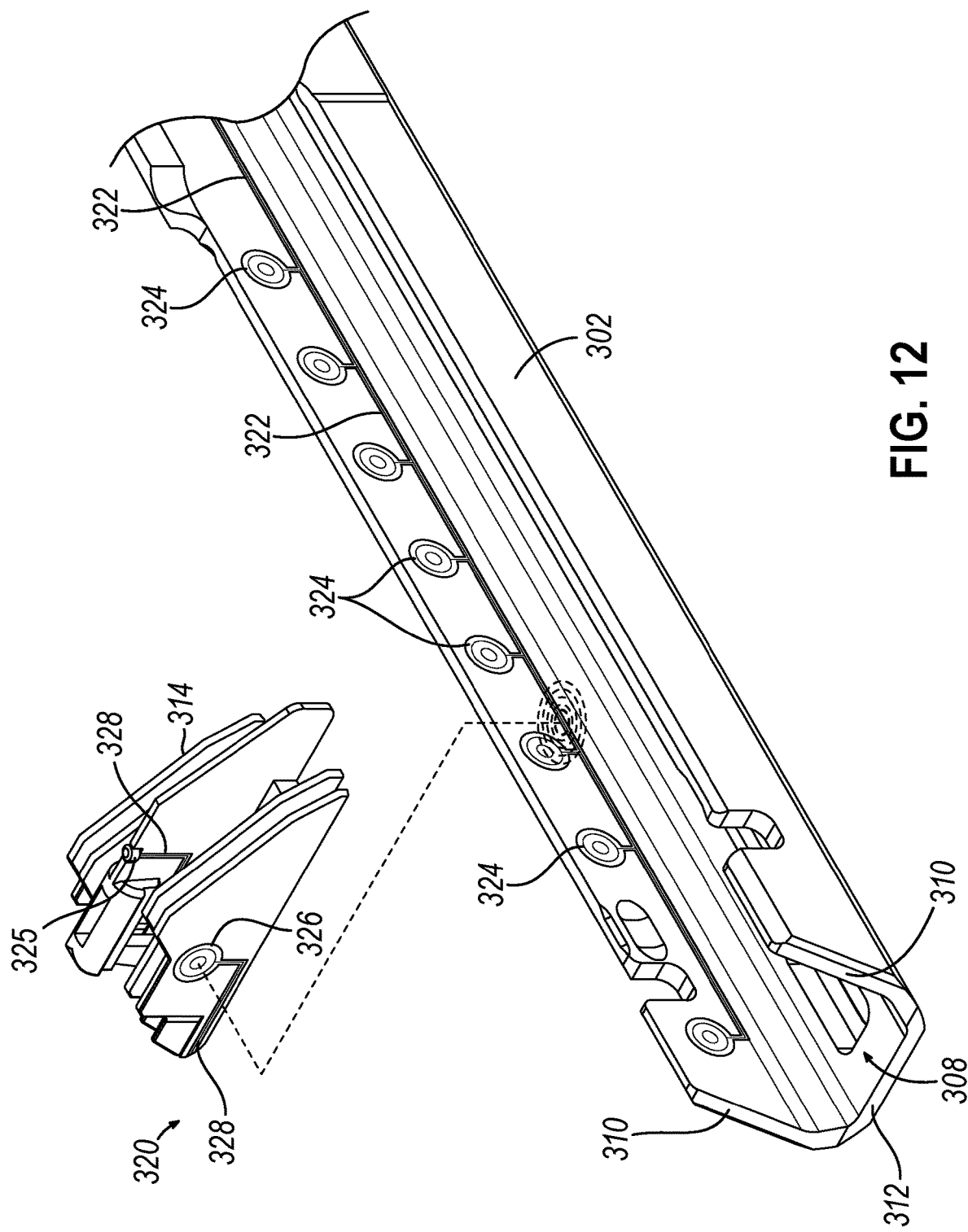
FIG. 12 depicts a perspective view of a lower jaw and wedge sled of a third exemplary end effector, with select portions of the third exemplary end effector omitted to reveal internal features, the lower jaw and wedge sled having illumination features.
Figure 13:
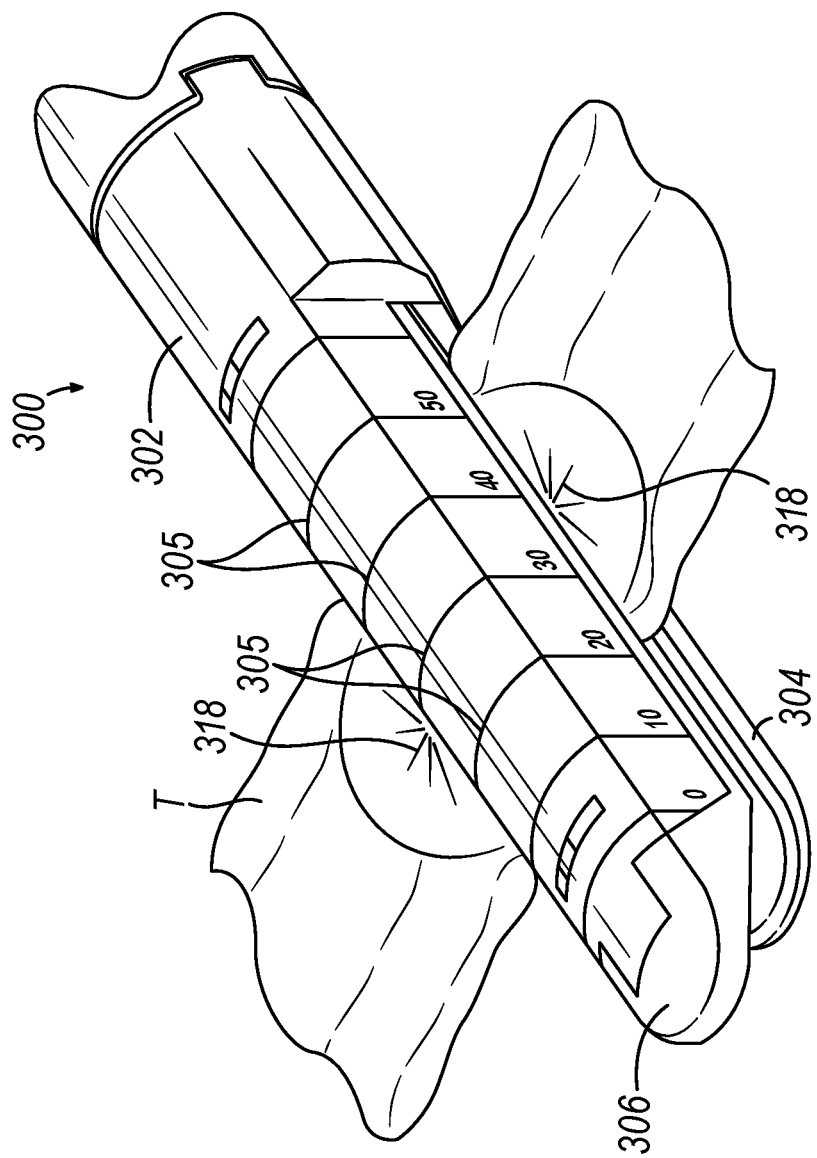
FIG. 13 depicts a perspective view of the third exemplary end effector of FIG. 12, shown clamping a tissue with the illumination features illuminated.

FIG. 13 shows an exemplary end effector (300) that may be readily incorporated into instrument (110) described above in replacement of either end effector (116, 210). End effector (300) is substantially similar to end effector (116, 210) described above, with differences elaborated below. In particular, as shown in FIG. 12, end effector (300) includes an illumination assembly (320) configured to illuminate to thereby visually represent the progression of wedge sled (314) actuating through jaws (302, 304) of end effector (300).

End effector (300) includes a lower jaw (302), an upper jaw (304), and a removable staple cartridge (306); which may be substantially similar to lower jaw (152, 212), upper jaw (150, 214), and staple cartridge (154, 218), respectively, with difference elaborated herein. As best seen in FIG. 12, lower jaw (302) includes a pair of side walls (310) coupled to each other by a base (312). Side walls (310) and base (312) together define a cartridge receiving channel (308) dimensioned to selectively couple with staple cartridge (306). As also best seen in FIG. 12, staple cartridge (306) includes wedge sled (314), which may be substantially similar to wedge sled (170, 238) described above, with difference elaborated below. Therefore, during the firing process, wedge sled (314) may actuate along a longitudinal path within staple cartridge (306) relative to lower jaw (302) such that end effector (300) may staple and sever tissue (T) in accordance with the description herein.

Lower jaw (302) includes an array of indicator markers (305). Indicator markers (305) are located along discrete longitudinal locations of lower jaw (302) and include a specific value associated with each marker (i.e., the 50 mm marker, the 40 mm marker, the 30 mm marker, etc.). The specific number associated with each marker (305) represents the distance that wedge sled (314) and/or the associated knife member (not shown) needs to travel further in order to complete the firing processes. For example, when wedge sled (314) and/or the associated knife member (not shown) is adjacent to the 20 mm indicator marker (305), wedge sled (314) still needs to travel 20 mm distally in order to complete the firing processes. As another example, when wedge sled (314) and/or the associated knife member (not shown) is adjacent to the 0 mm indicator marker (305), wedge sled (314) has reached the distal end of the firing process.

In the current example, wedge sled (314) and lower jaw (302) together form an illumination assembly (320). A portion of lower jaw (302) defining channel (308) includes a linear array of electromagnetic coils (324), each coupled to flex circuit wiring (322). Additionally, wedge sled (314) includes its own electromagnetic coil (326) and a light (325) coupled to each other via circuit wiring (328).

Flex circuit wiring (322) is configured to communicate electrical power to electromagnetic coils (324) such that coils (324) may suitably emit wireless energy for wireless power transfer to electromagnetic coil (326) of wedge sled (314). Linear array of electromagnetic coils (324) are configured to wirelessly transfer energy to electromatic coil (326) of wedge sled (314) such that light (325) may emit an illumination (318) (see FIG. 13) that may be viewed from the outside of jaws (302, 304). Since wedge sled (314) is housed within a body of removable staple cartridge (306), the wireless transfer of energy may allow the linear array of electromagnetic coils (326) to power light (325) even though coils (324, 326) are not in direct contact.

Linear array of electromagnetic coils (324) extends along a suitable length of lower jaw (304) such that electromagnetic coils (324) may suitably transfer wireless power to electromagnetic coil (326) of wedge sled (314) as wedge sled (314) travels within channel (308) to complete the firing process of severing and stapling tissue (T). Since light (325) is fixed to wedge sled (314), the illumination (318) provided by light (325) may provide a visual representation of where wedge sled (314) is located along the length of lower jaw (302), thereby indicating the progress wedge sled (314) has made in the firing process. This visual representation of illumination (318) may be captured by endoscope (28) and viewed on display (40) during exemplary use of the firing process.

Flex circuit wiring (322) extends proximally from lower jaws (302) and through other suitable components in order to couple with a power source in order to communicate electrical power to electromagnetic coils (324). In some instances, the power source may be housed within surgical instrument (110), while in other instances, flex circuit wiring (322) may be configured to couple with a power source when surgical instrument (110) is suitably coupled to robotic arm (42). Flex circuit wiring (322) may couple with a power source utilizing any suitable means as would be apparent to one skilled in the art in view of the teachings herein.

While wedge sled (314) and lower jaw (302) form illumination assembly (320) in the current example, it should be understood that any other suitable components may form illumination assembly (320) as would be apparent to one skilled in the art in view of the teachings herein. For instance, any component that actuates with wedge sled (314) may include the illumination features associated with wedge sled (314) in the current example, while any component that remains substantially stationary relative to lower jaw (302) (such as upper jaw (304) or shaft assembly (114)) during the firing process may be include the illumination features associated with lower jaw (302).

B. End Effector with Firing Assembly Position Tracker for Augmented Reality

In some instances, it may be desirable to visually represent the longitudinal location of pusher member (166), pusher block (236), and/or wedge sled (170, 238) within jaws (150, 152, 212, 214) by overlaying a digital representation of such components onto the image of jaws (150, 152, 212, 214) captured by endoscope (28) and shown in display (40). In other words, it may be desirable to augment the images shown on display (40) of jaws (150, 152, 212, 214) stapling and severing (T) with a visual representation of pusher member (166), pusher block (236), and/or wedge sled (170, 238) relative to the capture image of jaws (150, 152, 212, 214) during the exemplary firing process.

Figure 14:
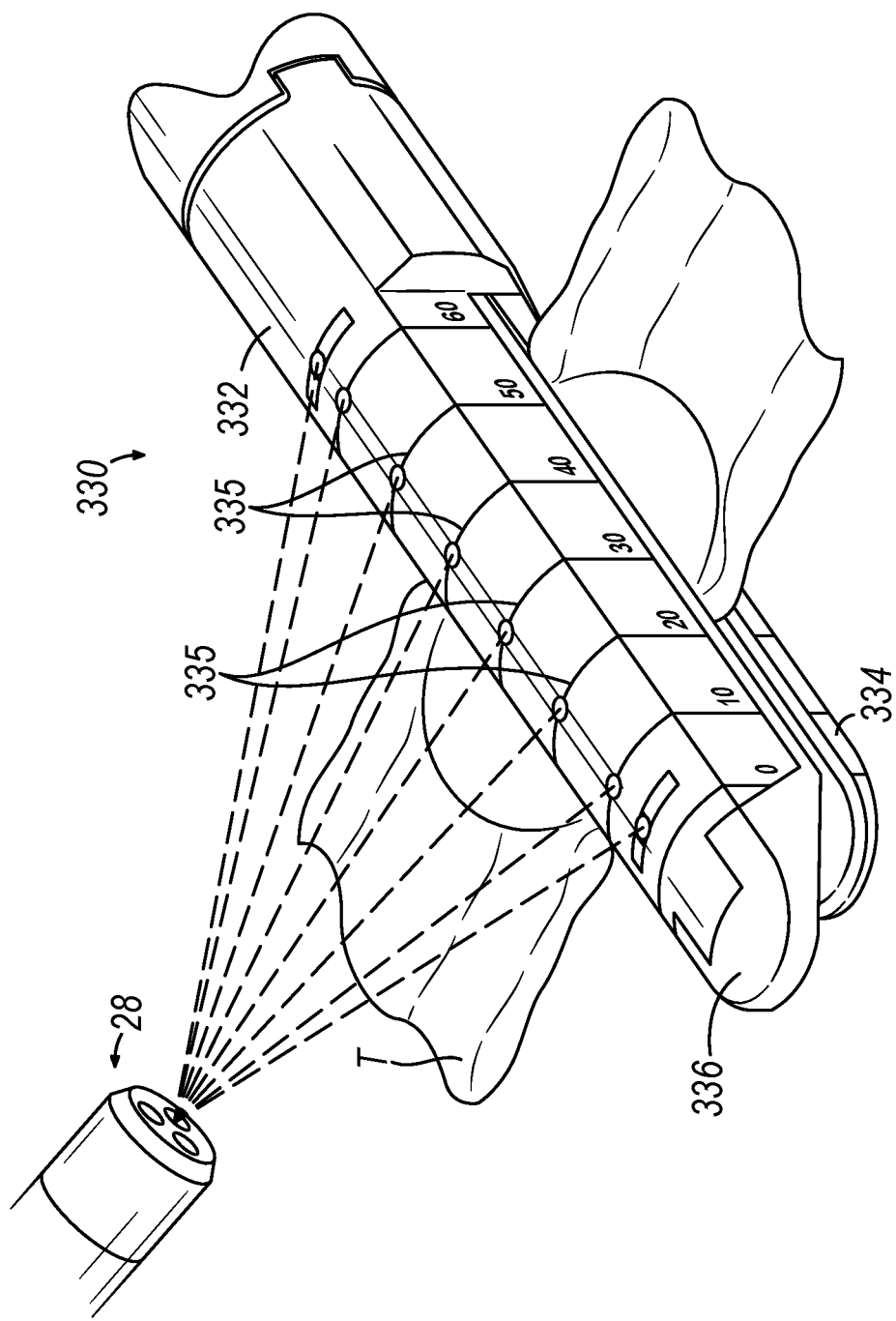
FIG. 14 depicts a perspective view of a fourth exemplary end effector, shown clamping a tissue with a second configuration of illumination features illuminated.
Figure 15:
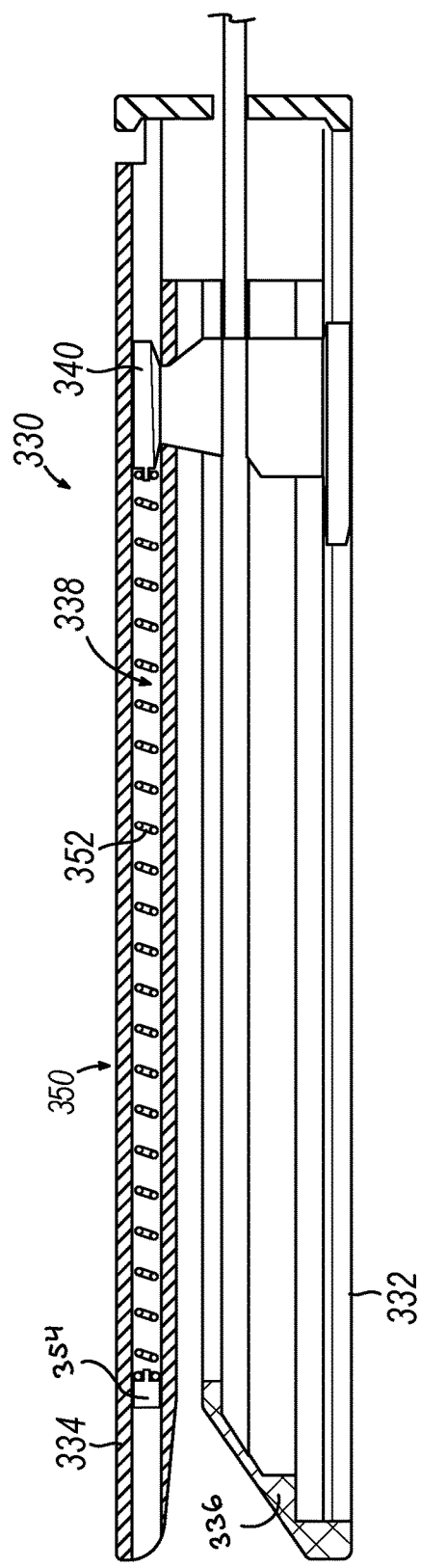
FIG. 15 depicts a cross-sectional side view of the end effector of FIG. 14.
Figure 16:
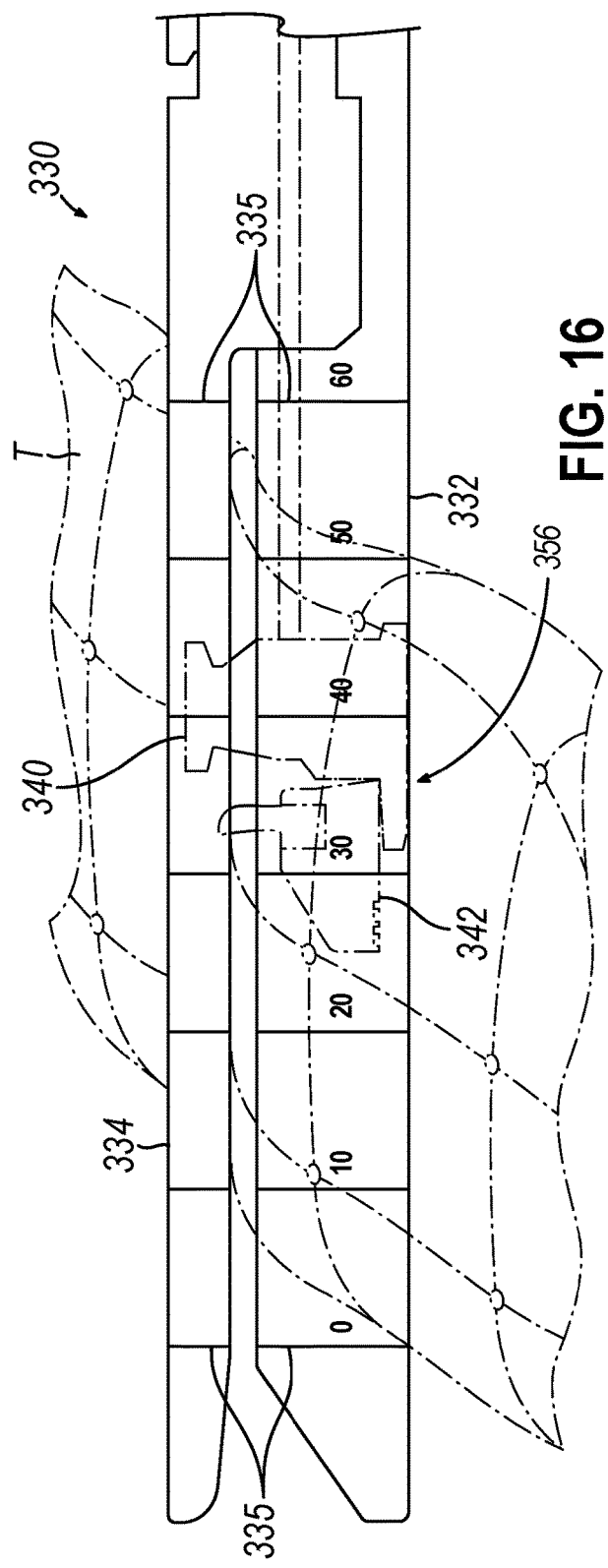
FIG. 16 depicts a side view of the end effector of FIG. 14 in use and clamping a tissue, the tissue shown as transparent, with select internal portions of the end effector overlayed for functional clarity.

FIGS. 14-15 show an exemplary end effector (330) while FIG. 16 shows an image captured by endoscope (28) and shown on display (40) with an augmented projection (356) of pusher member (340) and wedge sled (342) during the firing process. As will be described in greater detail below, end effector (330) may be used in conjunction with endoscope (28), display (40), and processor (38) to track the longitudinal position of a pusher member (340) and wedge sled (342) during the firing process and digitally project that longitudinal position onto images of jaws (332, 334) shown on display (40).

End effector (330) includes a lower jaw (332), an upper jaw (334), and a removable staple cartridge (336); which may be substantially similar to lower jaw (152, 212), upper jaw (150, 214), and staple cartridge (154, 218), respectively, with difference elaborated herein. As best seen in FIG. 16, end effector (330) further includes a pusher member (340) while staple cartridge (336) includes wedge sled (342), which may be substantially similar to pusher member (166, 236) and wedge sled (170, 238) described above, respectively with difference elaborated below. Therefore, during the firing process, pusher member (340) and wedge sled (342) may actuate along a longitudinal path relative to jaws (332, 334) such that end effector (330) may staple and sever tissue (T) in accordance with the description herein.

Jaws (332, 334) include an array of indicator markers (335). Indicator markers (335) are located along discrete longitudinal locations of jaws (302, 304) and include a specific value associated with each marker (i.e., the 50 mm marker, the 40 mm marker, the 30 mm marker, etc.). The specific number associated with each marker (335) represents the distance that pusher member (340) and wedge sled (342) need to travel further in order to complete the firing processes. Endoscope (28) may capture images of indicator markers (335) such that processor (38) may utilize markers (335) in a visualization system as reference points. As will be described in greater detail below, processor (38) may utilize these reference points provided by markers (335), as well as data provided by linear displacement sensor assembly (350), in order to accurately project an augmented reality projection of pusher member (340) and wedge sled (342) relative to jaws (332, 334). Markers (335) may include any suitable components as would be apparent to one skilled in the art in view of the teachings herein.

As best shown in FIG. 15, end effector (330) includes a linear displacement sensor assembly (350). Linear displacement sensor assembly (350) is configured to measure the linear displacement to pusher member (340) relative to jaws (332, 334) during the firing process. Further, linear displacement sensor assembly (350) is in communication with processor (38) such that linear displacement sensor assembly (350) may communicate the measured linear displacement of pusher member (340) relative to jaws (332, 334) to processor (38). Processor (38) may utilize this information to digitally project an augmented reality projection (356) of pusher member (340) and wedge sled (342) onto images captured by endoscope (28) and shown on display (40) such that a user may track the progression of pusher member (340) and wedge sled (342) during the firing process.

In the current example, linear displacement sensor assembly (350) includes a spring (352) and a linear variable displacement transducer "LVDT" (354). Spring (352) is housed within a longitudinal slot (338) of upper jaw (334). Longitudinal slot (338) may be substantially similar to longitudinal slot (186, 234) described above, with difference elaborated below. Therefore, longitudinal slot (338) is dimensioned to receive a flange of pusher member (340) during the firing process.

A proximal end of spring (352) is fixed to the flange of pusher member (340) configured to actuate within slot (338) of upper jaw (332), while a distal end of spring (352) is suitably coupled to LVDT (354). LVDT (354) is coupled to a distal end of upper jaw (334) within longitudinal slot (338). As pusher member (340) actuates distally relative to jaws (332, 334), spring (352) may compress between pusher member (340) and LVDT (354). Conversely, as pusher member (340) actuates proximally relative to jaws (332, 334), spring (352) may expand between pusher member (340) and LVDT (354).

LVDT (354) may measure the longitudinal position of pusher member (340) due to the change in length of spring (352) during the firing process of pusher member (340). LVDT (354) is in communication with processor (38) such that LVDT (354) may communicate the measured linear displacement of pusher member (340) relative to jaws (332, 334) to processor (38). Processor (38) may utilize this information provided by LVDT (354), along with the reference points provided by markers (335) captured by endoscope (28), in order to accurately project an augmented reality projection (356) of pusher member (340) and wedge sled (342) relative to jaws (332, 334) during the firing process. Therefore, the operator may track the progress of pusher member (340) and wedge sled (342) during the firing process via an approximated augmented reality projection (356).

While in the current example, spring (352) and LVDT (354) are used to track the linear displacement of pusher member (340) and communicate that linear displacement to processor (38), any other suitable means may be utilized to track and communicate the linear dispatchment of pusher member (340) relative to jaws (332, 334) as would be apparent to one skilled in the art in view of the teachings herein. For instance, the portion of robotic arm (42) configured to drive movement of pusher member (340) may have an encoder configured to monitor the rotational displacement of the portion of robotic arm (42) configured to drive pusher member (340), therefore allowing the encoder to monitor the position of pusher member (340) relative to jaws (332, 334). Such an encoder may be in communication with processor (38) such that processor (38) may utilize information provided by encoder in order to project an augmented reality projection (356) onto images captured by endoscope (28) and shown on display (40).

Figure 17A:
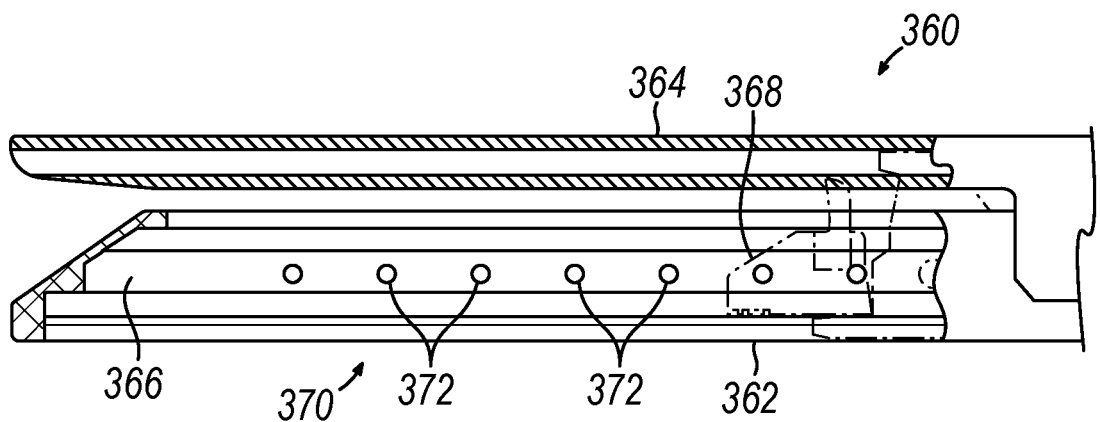
FIG. 17A depicts a cross-sectional side view of a fifth exemplary end effector with the upper jaw and lower jaw in a closed position, shown with select internal portions of the end effector in a first staple firing position and overlayed for functional clarity, shown with a third configuration of illumination features not illuminated.
Figure 17B:
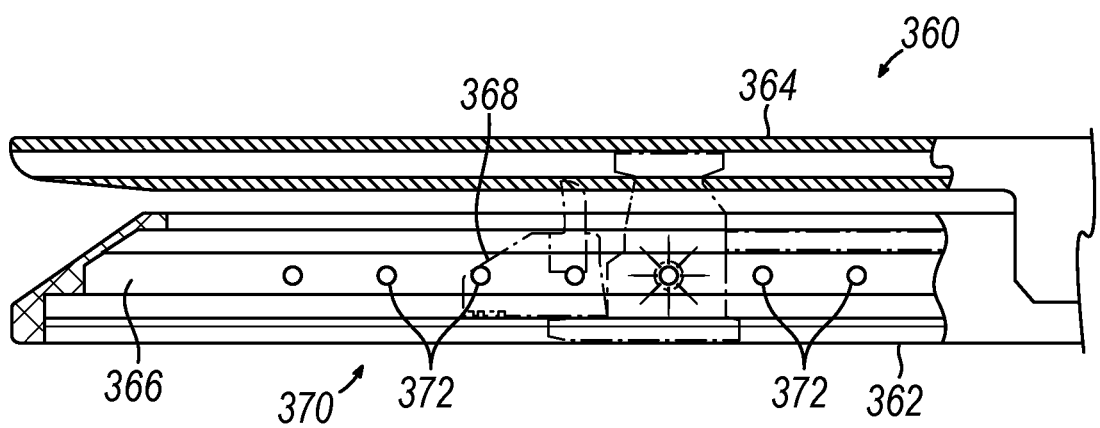
FIG. 17B depicts a cross-sectional side view of the fifth exemplary end effector of FIG. 17A with the upper jaw and lower jaw in a closed position, shown with select internal portions of the end effector in a second staple firing position and overlayed for functional clarity, shown with the third configuration of illumination features illuminated.
Figure 17C:
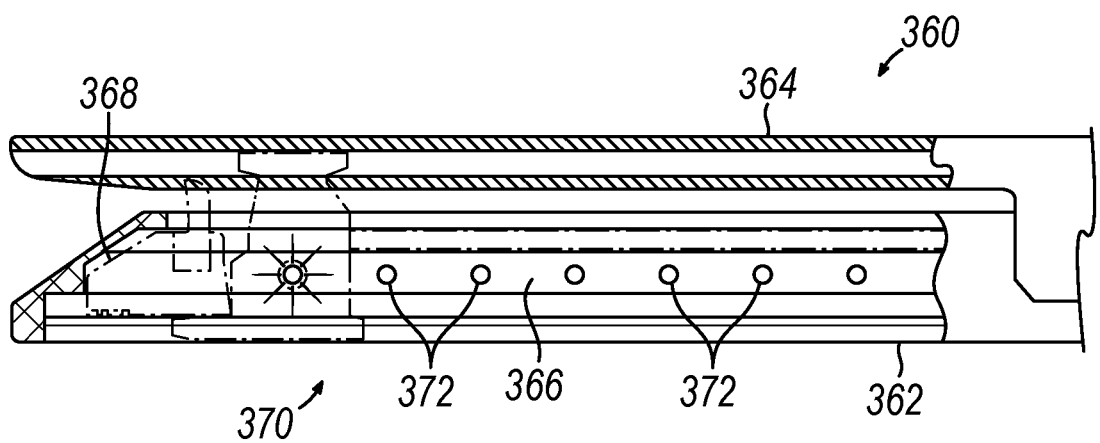
FIG. 17C depicts a cross-sectional side view of the fifth exemplary end effector of FIG. 17A with the upper jaw and lower jaw in a closed position, shown with select internal portions of the end effector in a third staple firing position and overlayed for functional clarity, shown with the third embodiment of illumination features illuminated.

C. End Effectors and Shaft Assemblies with Various Position Tracking Features for Firing Assemblies FIGS. 17A-17C show an exemplary end effector (360) that may be readily incorporated into instrument (110) described above in replacement of either end effector (116, 210). End effector (360) is substantially similar to end effector (116, 210) described above, with differences elaborated below. In particular, end effector (360) includes an illumination assembly (370) comprising a linear array of lights (372) configured sequentially illuminate to thereby visually represent the progression of wedge sled (368) actuating through jaws (362, 364) of end effector (360).

Figure 18:
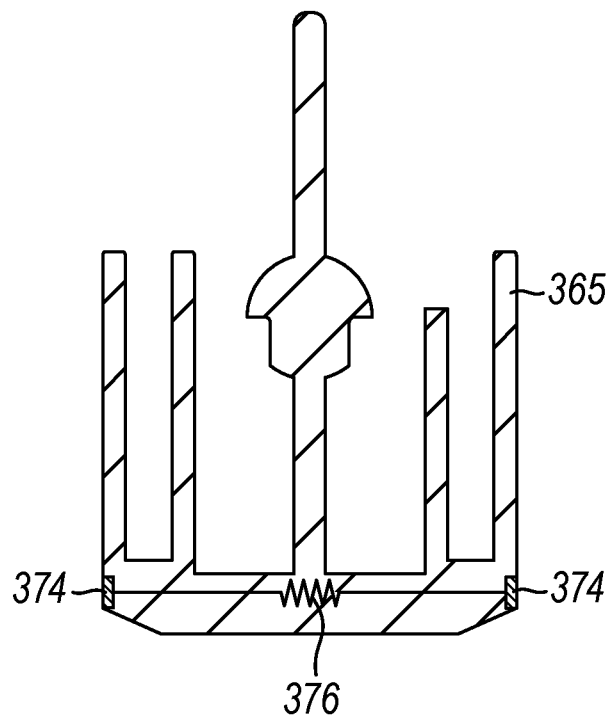
FIG. 18 depicts an end view of a wedge sled of the fifth exemplary end effector of FIG. 17A, with select portions of the third exemplary end effector omitted.

End effector (360) includes a lower jaw (362), an upper jaw (364), and a removable staple cartridge (366); which may be substantially similar to lower jaw (152, 212), upper jaw (150, 214), and staple cartridge (154, 218), respectively, with difference elaborated herein. As best seen in FIG. 18, staple cartridge (366) includes wedge sled (368), which may be substantially similar to wedge sled (170, 238) described above, with difference elaborated below. Therefore, during the firing process, wedge sled (368) may actuate along a longitudinal path within staple cartridge (366) relative to lower jaw (362) such that end effector (360) may staple and sever tissue (T) in accordance with the description herein.

Figure 19:
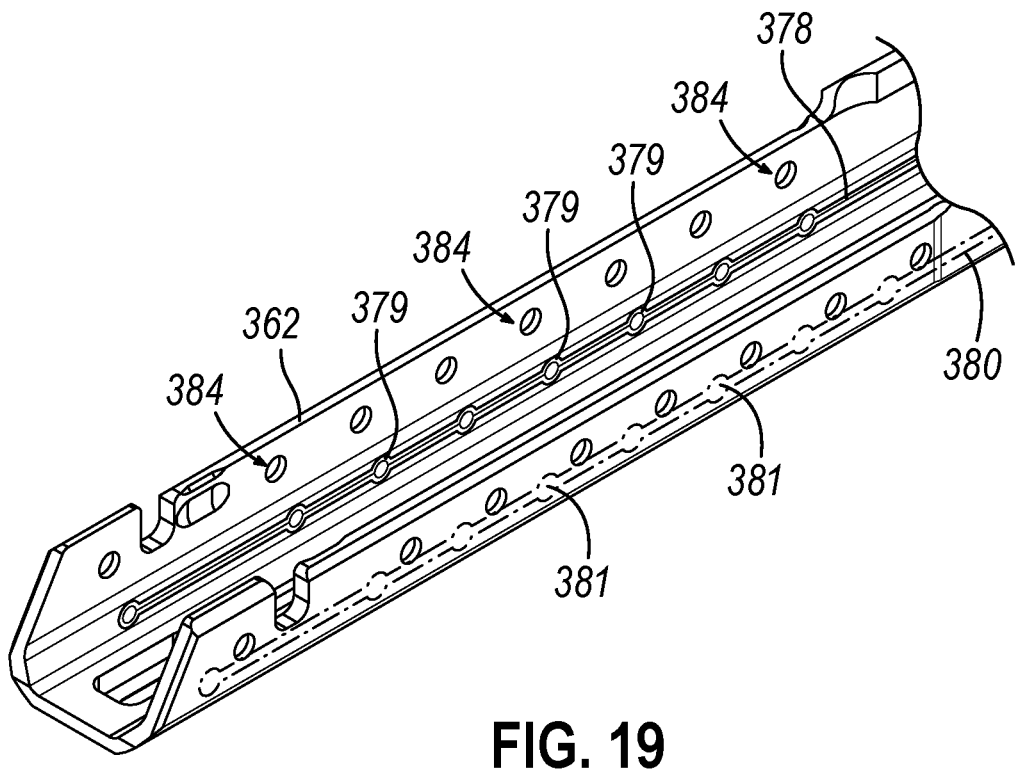
FIG. 19 depicts a perspective view of the lower jaw of the fifth exemplary end effector of FIG. 17A, with select portions of the fifth exemplary end effector omitted to reveal internal features.

In the current example, wedge sled (368) and lower jaw (362) together form an illumination assembly (370). As best shown in FIGS. 17A-17C, lower jaw (362) includes a linear array of lights (372) located on an outer surface of lower jaw (362). Therefore, as an individual light in the linear array of lights (372) illuminate in accordance with the description herein, such an illumination may be easily visible via endoscope (28). As shown in FIG. 19, the flanges of lower jaw (362) define a corresponding linear array of openings (384) dimensioned to house a respect light (372) of the linear array. Similar to lower jaw (302) described above, lower jaw (362) may include a plurality of indicator markers. Lights (372) may be located at a corresponding indicator marker such that illumination of an individual light (372) may signify the progress of wedge sled (368) being advanced through lower jaw (362) during the firing process.

As best shown in FIG. 19, illumination assembly (370) includes a first flex circuit (378) having a plurality of contacts (379) and a second flex circuit (380) also having a plurality of contacts (381). Each flex circuit (378, 380) extends along a length of jaw (362). One flex circuit (378, 380) may extend proximally to couple with a suitable power source, while contacts (379, 381) of the other flex circuit (378, 380) may be in communication with a respective light (372).

As best shown in FIG. 18, wedge sled (368) includes a pair a laterally presented contacts (374) that are electrically coupled to each other and a cartridge identifying resistor (376) interposed between contacts (374). Contacts (374) are located on wedge sled (368) such that when staple cartridge (366) is initially coupled with lower jaw (362), contacts (374) may be in communication with a proximal most contact (379, 381) of each flex circuit (378, 380). Therefore, wedge sled (368) may complete an electrically circuit with proximal most contacts (379, 381) of flex circuits (378, 380) when staple cartridge (366) is initially coupled to lower jaw (362). Resistor (376) may contain a specific resistance associated with the specific type of staple cartridge (366) being coupled with lower jaw (362). Therefore, robotic surgical system (10) may identify the type of staple cartridge (366) coupled with lower jaw (362) by reading the resistance value of resistor (376).

Additionally, as wedge sled (368) is actuated distally to staple and sever tissue, contacts (374) may complete an electrical circuit with adjacent contacts (379, 381) of flex circuits (378, 380). When specific contacts (379, 381) are electrically coupled by contacts (374) of sled (368), the individual light (372) associated with the specific contacts (279, 281) of flex circuits (378, 380) may illuminate, thereby indicting to a user where wedge sled (368) is relative to lower jaw (362). Once wedge sled (368) is advanced past individual contacts (379, 381), the circuit illuminating light (372) may no longer be formed such that light (372) is no longer illuminated. Therefore, illumination assembly (370) may be used to visually approximate the location of wedge sled (368), and therefore allow a user to monitor the progression of wedge sled (368) actuating relative to lower jaw (362).

Figure 20:
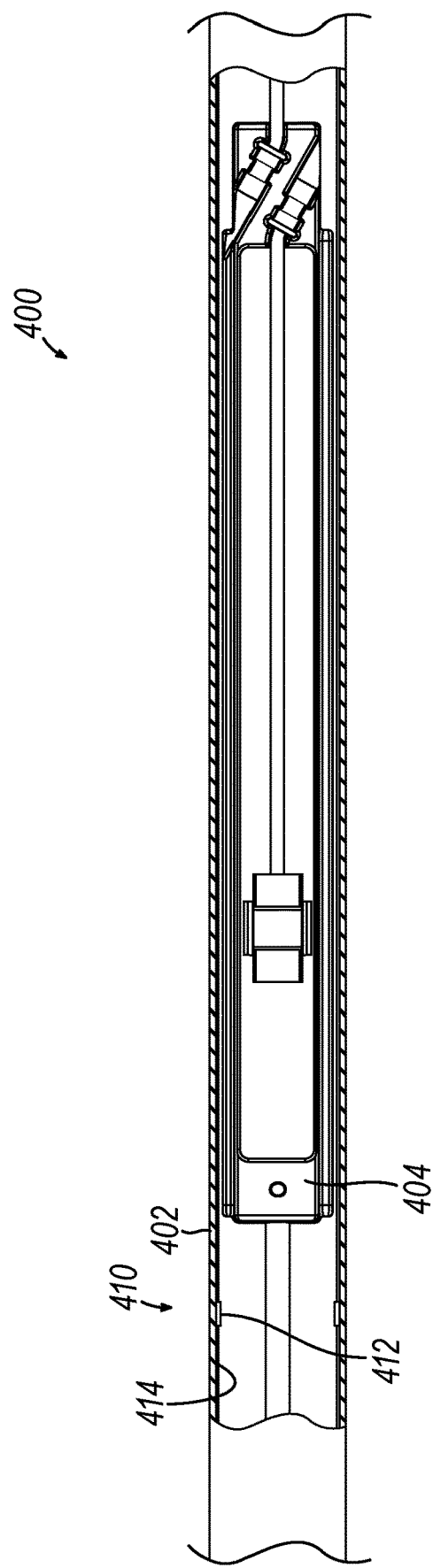
FIG. 20 depicts a top cross-sectional view of a second exemplary configuration of an elongate shaft of an alternative exemplary surgical instrument that may be used with the robotic surgical system of FIG. 1, the elongate shaft having a movable feature disposed therein and a fourth configuration of illumination features.
Figure 21A:
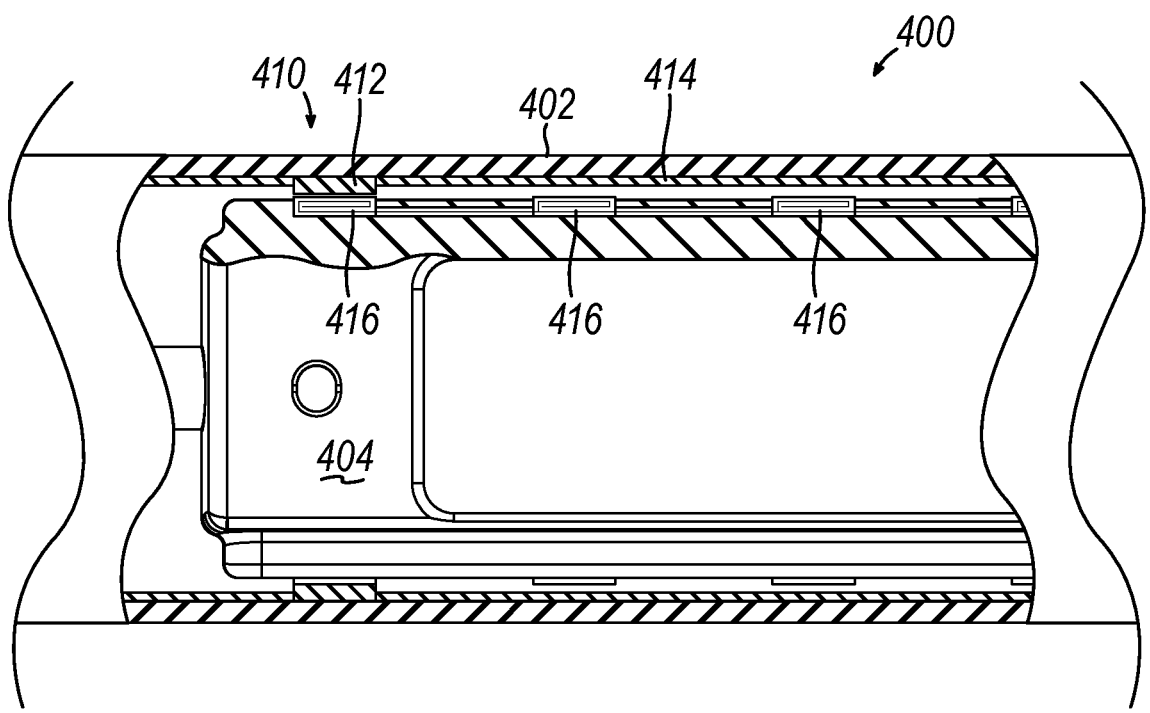
FIG. 21A depicts a cross-sectional top view of the elongate shaft of FIG. 20, with the movable feature in a first position.
Figure 21B:
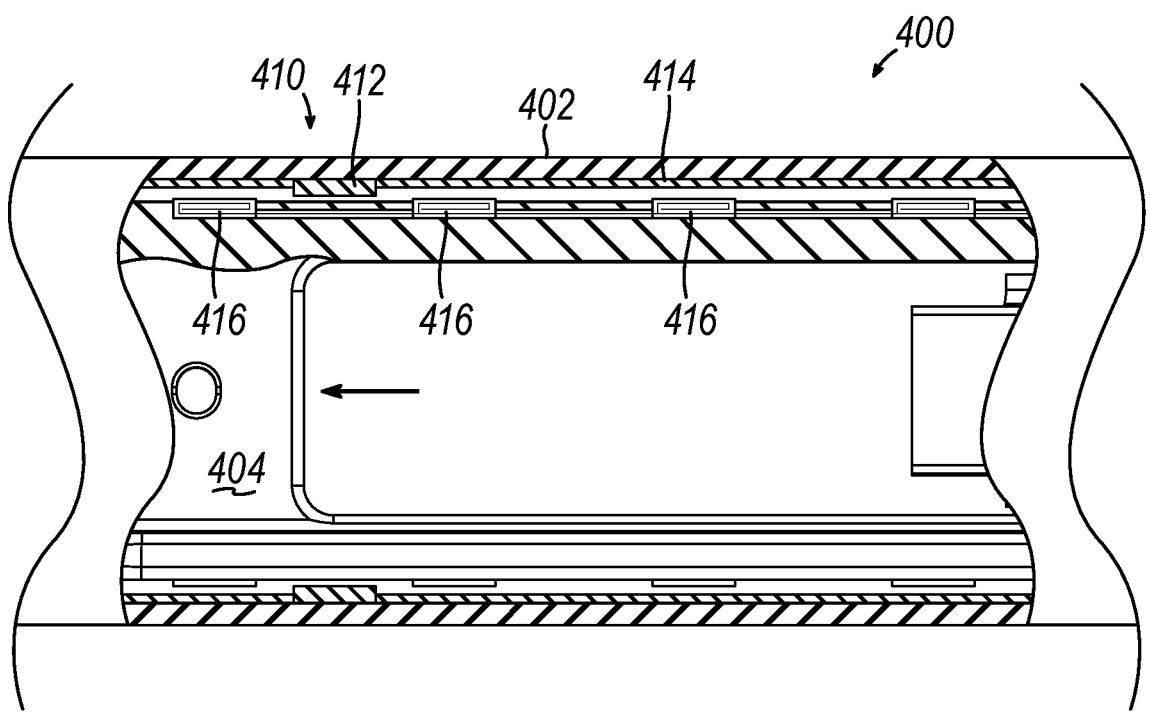
FIG. 21B depicts a cross-sectional top view of the elongate shaft of FIG. 20, with the movable feature in a second position.

In some instances, a portion of an illumination assembly may associate with the shaft assembly (114) rather than end effector (116). FIGS. 20-21B show a shaft (400) having an exemplary illumination activation assembly (410) configured to generate a signal in order to activate illumination features associated with the firing of any suitable end effector described herein. Shaft assembly (400) may be substantially similar to shaft assembly (114) described above, with differences elaborated below. Shaft assembly (400) includes a stationary portion (402) and a translating shuttle (404). Translating shuttle (404) is configured to actuate within stationary portion (402) to thereby actuate any suitable firing mechanism(s), (e.g., wedge sled (170, 238)). Therefore, the longitudinal position of translating shuttle (404) relative to stationary portion (402) may correspond to the progression as which any suitable end effector is firing to staple and sever tissue in accordance with the description herein.

Illumination activation assembly (410) includes a magnetic sensor (412) and flex circuit wiring (414), both associated with stationary portion (402). Flex circuit wiring (414) is electrically coupled with magnetic sensor (412). Flex circuit wiring (414) extends proximally and couples with a suitable power source and/or processing unit. Flex circuit wiring (414) extends distally and is coupled to an illumination assembly, such as any suitable illumination assembly described herein. Additionally, illumination activation assembly (410) includes an array of magnets (416) longitudinally disposed on translating shuttle (404).

Figure 22:
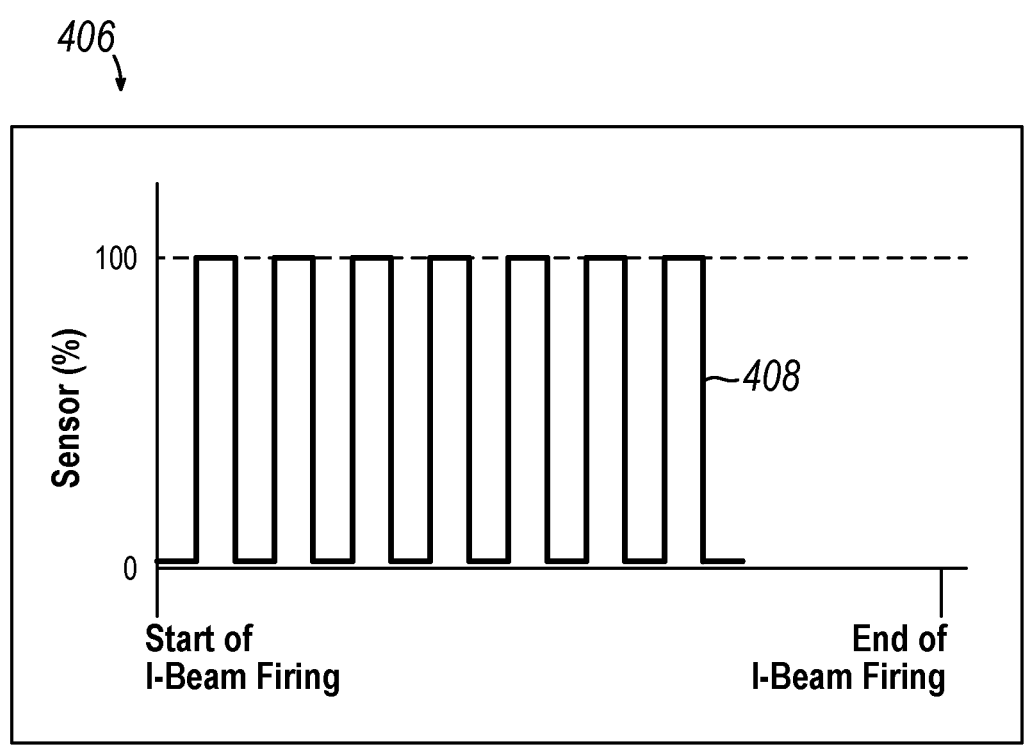
FIG. 22 depicts a graphical representation of the output of the fourth configuration of illumination features during a staple firing stroke.

Magnets (416) are suitably adjacent to magnetic sensor (412) such that when shuttle (404) actuates during the firing process, an individual magnet (416) may be directly under magnetic sensor (412) without physically contacting sensor (412). When an individual magnetic (416) is directly under magnetic sensor (412), as shown in FIG. 21A, magnetic sensor (412) may generate a signal and transfer that signal to suitable illumination features of instrument (10). When an individual magnet (416) is not directly under magnetic sensor (412), as shown in FIG. 21B, magnetic sensor (412) fails to generate a signal. Therefore, as shown in the graph (406) of FIG. 22, a signal generation line (408) alternates between generating a signal and not generating a signal as shuttle (404) actuates within stationary portion (402).

Magnets (416) are disposed on shuttle (404) in order to generate a signal in magnetic sensor (412) as shuttle (404) fires end effector (116, 210) in accordance with the description herein. Magnets (416) are strategically placed on shuttle (404) such that the signal generated by sensor (412) may be indicative of the progression at which end effector (116, 210) is being fired to staple and sever tissue. Signals generated by magnetic sensor (412) may be used in conjunction with any suitable illumination assembly described herein to light such an illumination assembly, thereby tracking the progression as which shuttle (404) fires end effector (116, 210).

Figure 23:
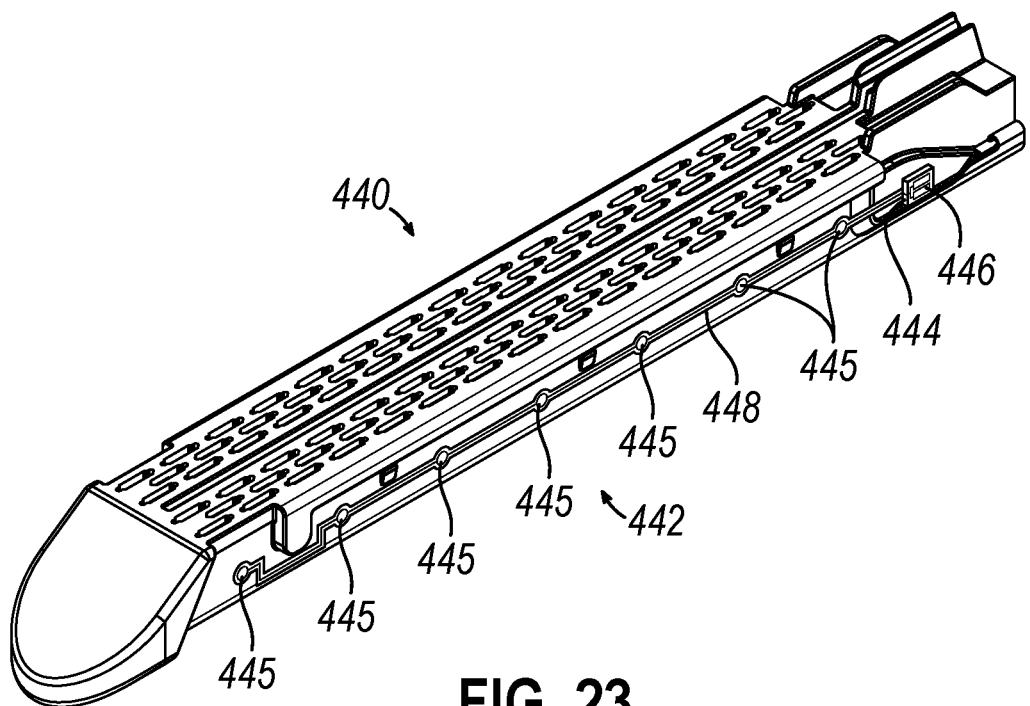
FIG. 23 depicts a perspective view of a staple cartridge of a sixth exemplary end effector, with select portions of the sixth exemplary end effector omitted, the staple cartridge having a fifth configuration of illumination features.

FIG. 23 shows an exemplary replaceable staple cartridge (440) having an illumination assembly (442) that may be used in conjunction with shaft assembly (400) described above. Illumination assembly (442) includes an electrical chip (444) having a counter functionality, a flex circuit (448) extending along a length of the body of staple cartridge (440), and a longitudinal array of lights (445) disposed on an outer surface of replaceable staple cartridge (440). The longitudinal array of lights (445) are electrically coupled to electrical chip (444) via flex circuit (448).

Electrical chip (444) includes electrical contacts (446) which may selectively couple with corresponding electrical contacts on a lower jaw of end effector. Corresponding electrical contacts on the lower jaw may be in electrical communication with a proximal end of flex circuit (414) extending within stationary portion (402) of shaft assembly (400). Therefore, when replaceable staple cartridge (440) is coupled with a suitable lower jaw, flex circuit (414) may communicate signals generated by illumination activation assembly (410) to electrical chip (444).

Longitudinal array of lights (445) may be exposed to an outer surface of lower jaw via a complementary array of openings defined by lower jaw when cartridge (440) is suitably coupled to lower jaw. Therefore, as lights (445) become illuminated, they may be easily viewed via endoscope (28).

As mentioned above, electrical chip (444) has a counter functionality. Therefore, electrical chip (444) may count the number of times illumination activation assembly (410) transmits a signal in accordance with the description herein. As mentioned above, signals generated by sensor (412) may be indicative of the progression at which end effector (116, 210) is being fired to staple and sever tissue. Lights (445) may be selectively placed along the length of staple cartridge (440) in order to represent or approximate the location of a wedge sled of staple cartridge (440) as shuttle (404) drives wedge sled distally. Electrical chip (444) may activate and/or deactivate lights (445) based on the number of signals counted by electrical chip (444).

For example, if electrical chip (444) counts one signal being received during the firing process, electrical chip (444) may activate the most proximal light (445). The most proximal light (445) may be placed along a location that approximates the location of wedge sled of cartridge (440) when electrical chip (444) counts the first signal. As another example, if electrical chip (444) counts a second signal being received during the firing process, electrical chip (444) may activate the second most proximal light (445). The second most proximal light (445) may be placed along a location that approximates the location of the wedge sled of cartridge (440) when electrical chip (444) counts the second signal. In some instances, once a light (445) is activated, chip (444) may keep that specific light (445) activated until wedge sled of staple cartridge (440) is fully advanced, until the firing process is completed, or until any other suitable event that would be apparent to one skilled in the art in view of the teachings herein. Therefore, in some instances, the linear array of lights (445) may remain activated to visually approximate the length at which wedge sled has traveled during the firing process. In some instances, only one light (445) may be activated at a time, such that once the second light (445) is activated by chip (444), chip (444) deactivates the first light (445), and so on. Therefore, in some instances, the linear array of lights (445) may be sequentially activated to visually approximate the general position at which wedge sled is located during the firing process.

Figure 24:
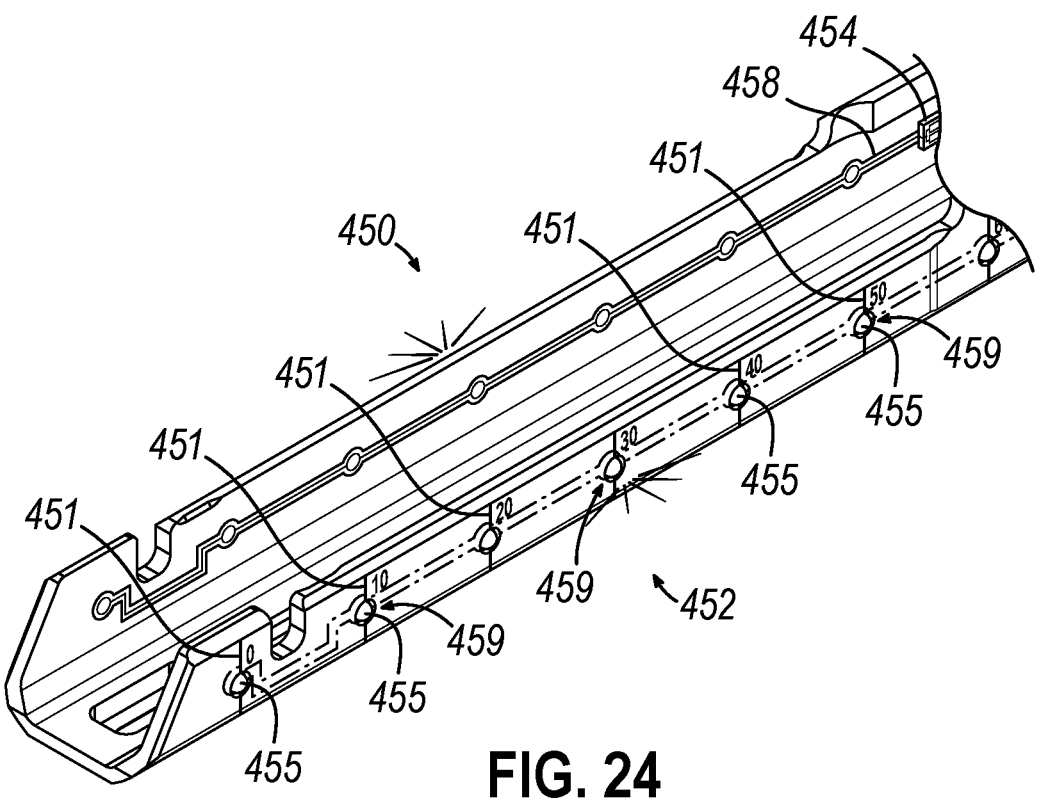
FIG. 24 depicts a perspective view of a lower jaw of a seventh exemplary end effector, with select portions of the seventh exemplary end effector omitted, the staple cartridge having a sixth configuration of illumination features.

FIG. 24 shows an exemplary lower jaw (450) having an illumination assembly (452) that may be used in conjunction with shaft assembly (400) described above. Illumination assembly (452) may be substantially similar to illumination assembly (442) described above, except components of illumination assembly (452) are associated with lower jaw (450) rather than a replaceable cartridge (440). Lower jaw (450) includes a plurality of indicator markers (451) that are substantially similar to indicator markers (305, 335) described above. Therefore, the specific number associated with each marker (451) represents the distance that a wedge sled and/or the associated knife member needs to travel further in order to complete the firing processes.

Illumination assembly (452) includes an electrical chip (454) having a counter functionality, a flex circuit (458) extending along a length of the body of lower jaw (450), and a longitudinal array of lights (455) disposed within openings (459) defined by flanges of lower jaw (450). The longitudinal array of lights (455) are coupled to electrical chip (454) via flex circuit (448).

Electrical chip (454) may be in electrical communication with a proximal end of flex circuit (414) extending within stationary portion (402) of shaft assembly (400). Therefore, flex circuit (414) may communicate signals generated by illumination activation assembly (410) to electrical chip (454).

As mentioned above, electrical chip (454) has a counter functionality. Therefore, electrical chip (454) may count the number of times illumination activation assembly (410) transmits a signal in accordance with the description herein. As mentioned above, signals generated by sensor (412) may be indicative of the progression at which end effector (116, 210) is being fired to staple and sever tissue. Lights (455) may be selectively placed along the length of lower jaw (450) with a corresponding indicator marker (451) in order to represent or approximate the location of a wedge sled as shuttle (404) drives wedge sled distally. Electrical chip (454) may activate and/or deactivate lights (455) based on the number of signals counted by electrical chip (454).

For example, if electrical chip (454) counts one signal being received during the firing process, electrical chip (454) may activate the most proximal light (455). The most proximal light (455) may be placed along a location that approximates the location of wedge sled of cartridge (440) when electrical chip (454) counts the first signal. As another example, if electrical chip (454) counts a second signal being received during the firing process, electrical chip (454) may activate the second most proximal light (455). The second most proximal light (455) may be placed along a location that approximates the location of the wedge sled when electrical chip (454) counts the second signal. In some instances, once a light (455) is activated, chip (454) may keep that specific light (455) activated until wedge sled is fully advanced, until the firing process is completed, or until any other suitable event that would be apparent to one skilled in the art in view of the teachings herein. Therefore, in some instances, the linear array of lights (455) may remain activated to visually approximate the length at which wedge sled has traveled during the firing process. In some instances, only one light (455) may be activated at a time, such that once the second light (455) is activated by chip (454), chip (454) deactivates the first light (455), and so on. Therefore, in some instances, the linear array of lights (455) may be sequentially activated to visually approximate the general position at which wedge sled is located during the firing process.

Figure 25A:
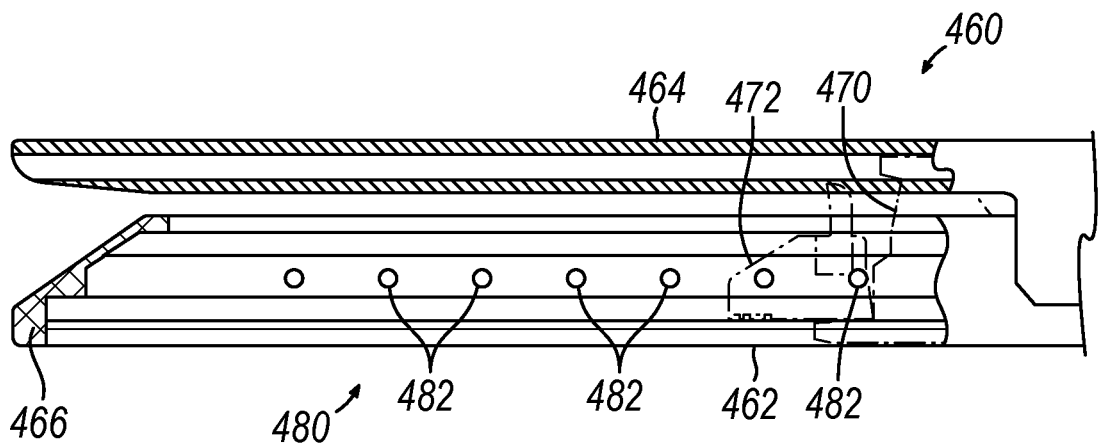
FIG. 25A depicts a cross-sectional side view of an eighth exemplary end effector with the upper jaw and lower jaw in a closed position, shown with select internal portions of the end effector in a first staple firing position and overlayed for functional clarity, shown with an seventh configuration of illumination features not illuminated.
Figure 25B:
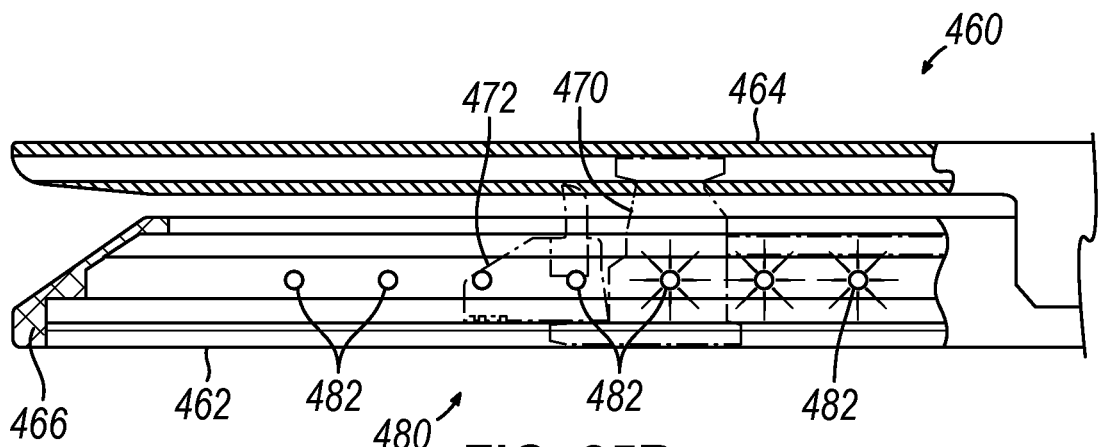
FIG. 25B depicts a cross-sectional side view of the eighth exemplary end effector of FIG. 25A with the upper jaw and lower jaw in a closed position, shown with select internal portions of the end effector in a second staple firing position and overlayed for functional clarity, shown with the seventh configuration of illumination features illuminated.
Figure 25C:
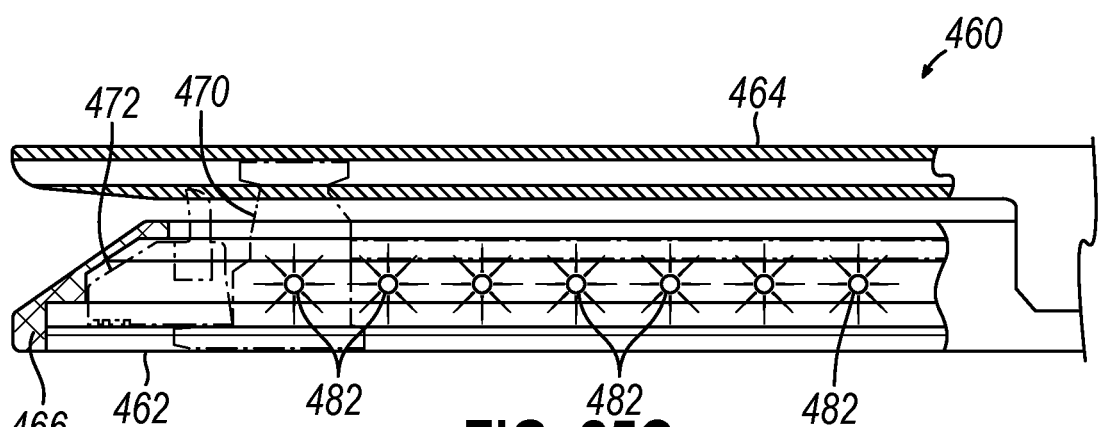
FIG. 25C depicts a cross-sectional side view of the eighth exemplary end effector of FIG. 25A with the upper jaw and lower jaw in a closed position, shown with select internal portions of the end effector in a third staple firing position and overlayed for functional clarity, shown with the seventh configuration of illumination features illuminated.

FIGS. 25A-25C show an exemplary firing of an exemplary end effector (460) in accordance with the teachings herein. End effector (460) includes a lower jaw (462), an upper jaw (464), a removable staple cartridge (466) having a wedge sled (472), a pusher member (470), and an illumination assembly (480) having a linear array of lights (482). Lower jaw (462), upper jaw (462), removable staple cartridge (466), wedge sled (472), and pusher member (470) may be substantially similar to lower jaw (152, 212), upper jaw (150, 214), removable staple cartridge (154, 218), wedge sled (170, 238), and pusher member/block (166, 236), described above, respectively, with differences elaborated below. Illumination assembly (480) may include any suitable other features of any illumination assembly (442, 452, 480, 510, 530) or illumination activation assembly (410, 430) described herein.

As shown in FIG. 25A-25C, as pusher member (470) and wedge sled (472) are advanced distally in order to complete the firing process of stapling and severing tissue, linear array of lights (482) begin to illuminate from the proximal most light (482) to the distal most light (482) in order to visually approximate the progress of wedge sled (472) stapling and severing tissue during the firing process. In particular, once a single light (482) is illuminated, that light (482) remains active during the distal actuation of pusher member (470). Therefore, the linear array of lights (482) may remain activated to visually approximate the length at which wedge sled (472) has traveled during the firing process.

Once pusher member (470) actuated wedge sled (472) to the distal most position, as shown in FIG. 25C, every light (482) is activated, thereby visually indicating to the operator that wedge sled (472) has reached the distal most position. In some instances, when pusher member is reacted, lights (482) may deactivate, sequentially from distal most light (482) to the proximal most light (482) in order to approximate the proximal retraction of pusher member (470) back to a pre-fired position.

Figure 26:
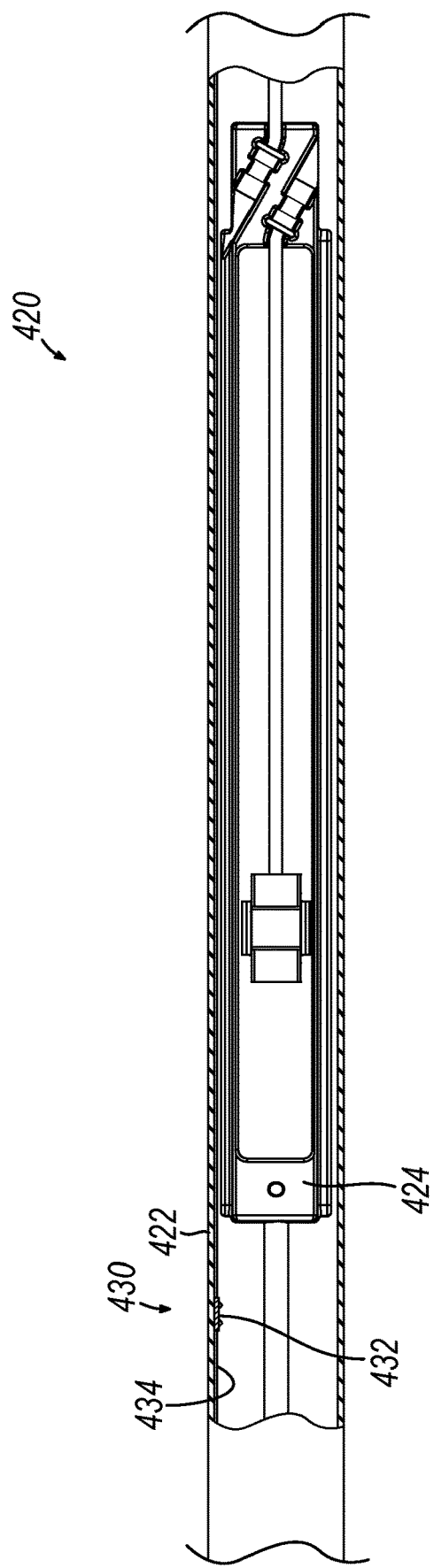
FIG. 26 depicts a top cross-sectional view of a third exemplary configuration of an elongate shaft of an alternative exemplary surgical instrument that may be used with the robotic surgical system of FIG. 1, the elongate shaft having a movable feature disposed therein and a eighth configuration of illumination features.
Figure 27A:
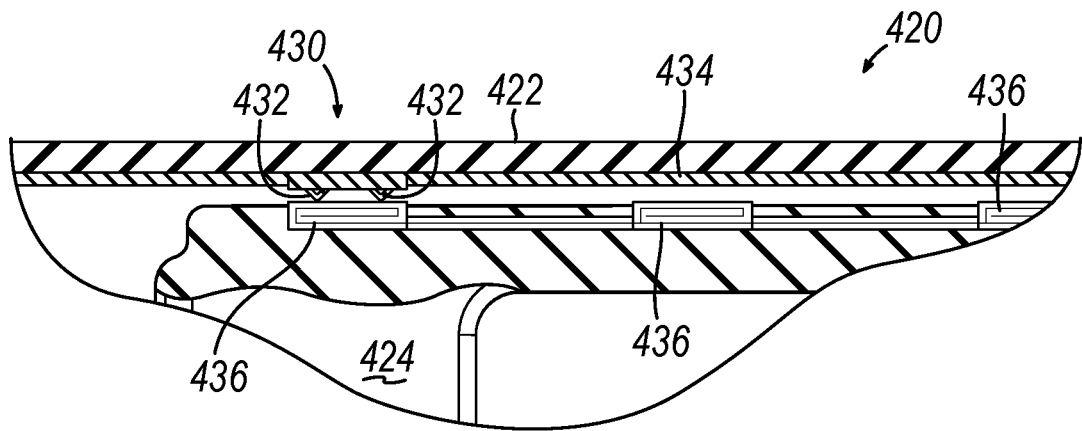
FIG. 27A depicts a cross-sectional top view of the elongate shaft of FIG. 26, with the movable feature in a first position.
Figure 27B:
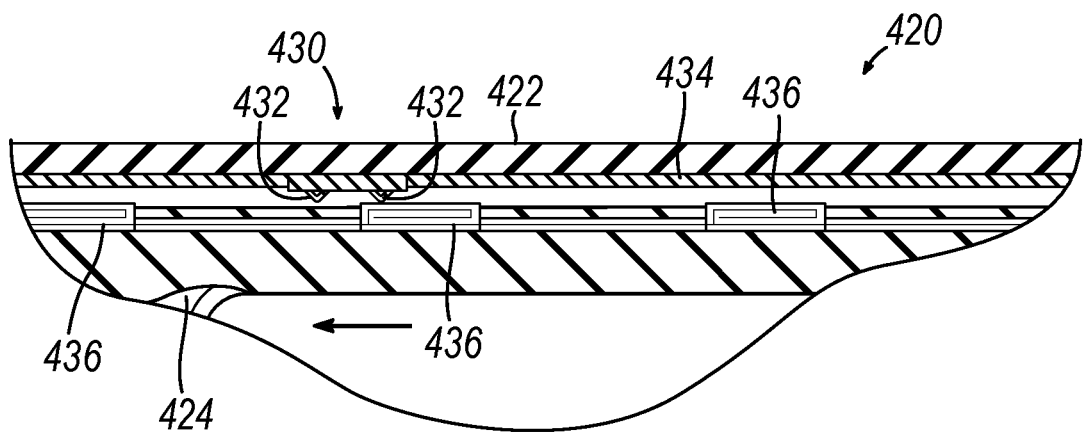
FIG. 27B depicts a cross-sectional top view of the elongate shaft of FIG. 26, with the movable feature in a second position.

FIGS. 26-27B show a shaft (420) having an exemplary illumination activation assembly (430) configured to generate a signal in order to activate illumination features associated with the firing of end effector (116). Therefore, shaft (420) may be used in replacement of shaft (400) described above in order to activate illumination assemblies (442, 452) described above. Shaft assembly (420) may be substantially similar to shaft assembly (114) described above, with differences elaborated below. Shaft assembly (420) includes a static body in the form of a stationary portion (422), and an actuating body in the form of a translating shuttle (424). Translating shuttle (424) is configured to actuate within stationary portion (422) to thereby actuate any suitable firing mechanism(s) (e.g., wedge sled (170, 238)). Therefore, the longitudinal position of translating shuttle (424) relative to stationary portion (422) may correspond to the progression at which any suitable end effector is firing to staple and sever tissue in accordance with the description herein.

Illumination activation assembly (430) includes a pair of stationary contacts (432) and flex circuit wiring (434), both associated with stationary portion (402). Flex circuit wiring (434) is electrically coupled with stationary contacts (432). Flex circuit wiring (434) extends proximally from stationary contacts (432) and couples with a suitable power source and/or processing unit. Flex circuit wiring (434) extends distally from stationary contacts (432) and is coupled to an illumination assembly, such as any suitable illumination assembly (442, 452) described herein. One stationary contact (432) is in electrical communication with the illumination assembly (442, 452) while the second electrical contact (432) is in electrical communication with the power source and/or processing unit. Stationary contacts (432) are normally electrically isolated from each other such that stationary contacts (432) provide a normally open circuit between illumination features and the power source and/or processing unit.

Additionally, illumination activation assembly (430) includes at least one contact body in the form of an array of actuating contacts (436) longitudinally disposed on translating shuttle (424). Actuating contacts (436) are suitably adjacent to stationary contacts (432) such that when shuttle (424) actuates during the firing process, individual contacts (436) come into direct contact with both stationary contacts (432). Once an individual contact (436) is in direct contact with both stationary contacts (432), both stationary contacts (432) are in electrically communication with each other such that the normally open electrical circuit is temporarily closed.

With stationary contacts (432) in electrical communication with each other, proximal portion of flex circuit (414) and a distal portion of flex circuit (414) are in electrical communication with each other. Therefore, stationary contacts (432) and individual actuating contacts (436) are configured to selectively close the circuit between illumination features and power source/processing unit in order to activate illumination features in accordance with the description herein. When an individual actuating contact (436) is in contact with both stationary contacts (432), as shown in FIG. 27A, the closed circuit may generate a signal and transfer that signal to suitable illumination features, such as illumination assemblies (442, 452) described above. When an actuating contact (436) is not directly in contact with both stationary contacts (432) as shown in FIG. 27B, stationary contacts (432) form an open circuit, thereby failing to generate a signal.

Actuating contacts (436) are disposed on shuttle (424) in order to generate a signal as shuttle (424) fires end effector (116, 210) in accordance with the description herein. Actuating contacts (436) are strategically placed on shuttle (424) such that the signal generated by closing the circuit via the connection between contacts (432, 436) may be indicative of the progression at which end effector (116, 210) is being fired to staple and sever tissue. Signals generated by the connection between contacts (432, 436) may be used in conjunction with any suitable illumination assembly (442, 452) thereby tracking the progression as which shuttle (424) fires end effector (116, 210).

In some instances, it may be desirable to visually track the approximate progress of the firing process to staple and sever tissue at a location other than the location of end effector. For example, it may be desirable to visually track the approximate progress of the firing process via indication markers and lights located on a portion of shaft assembly.

Figure 28:
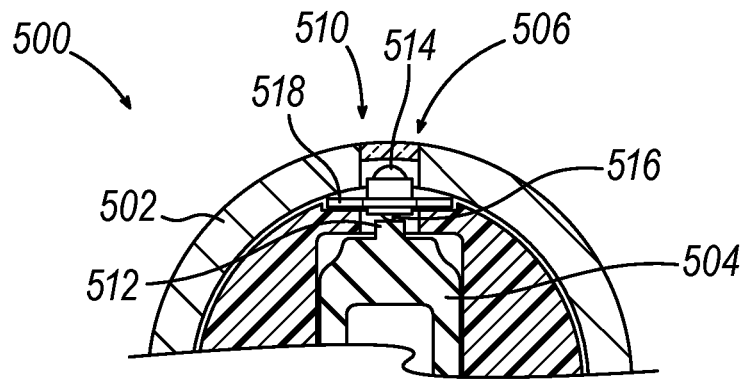
FIG. 28 depicts an end cross-sectional view of a portion of a fourth exemplary configuration of an elongate shaft of an alternative exemplary surgical instrument that may be used with the robotic surgical system of FIG. 1, the elongate shaft having a movable feature disposed therein and a ninth configuration of illumination features.
Figure 29:
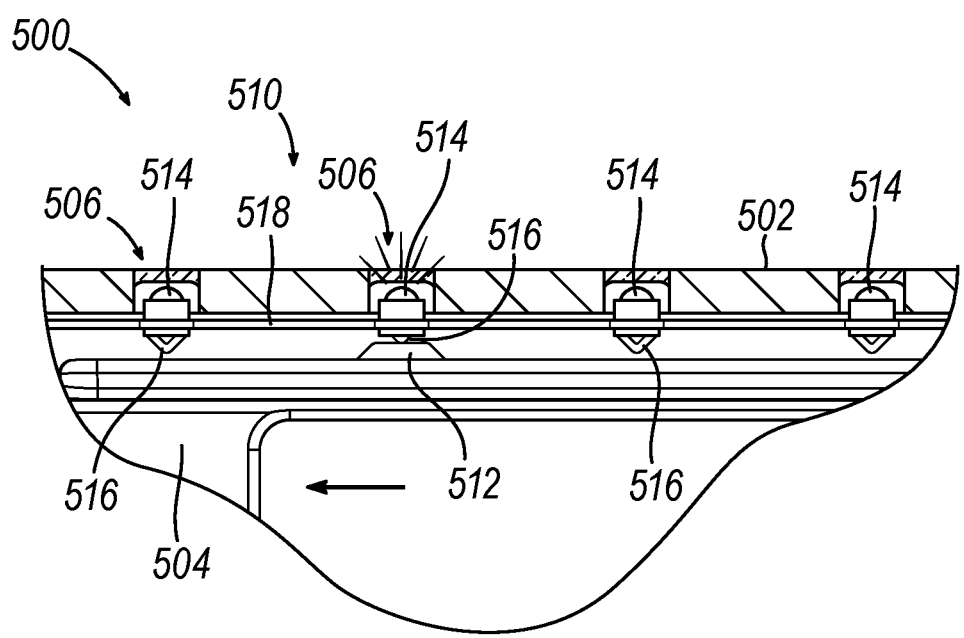
FIG. 29 depicts a side cross-sectional view of a portion of the elongate shaft of FIG. 28, shown with a portion of the ninth configuration of illumination features in an illuminated state.
Figure 30:
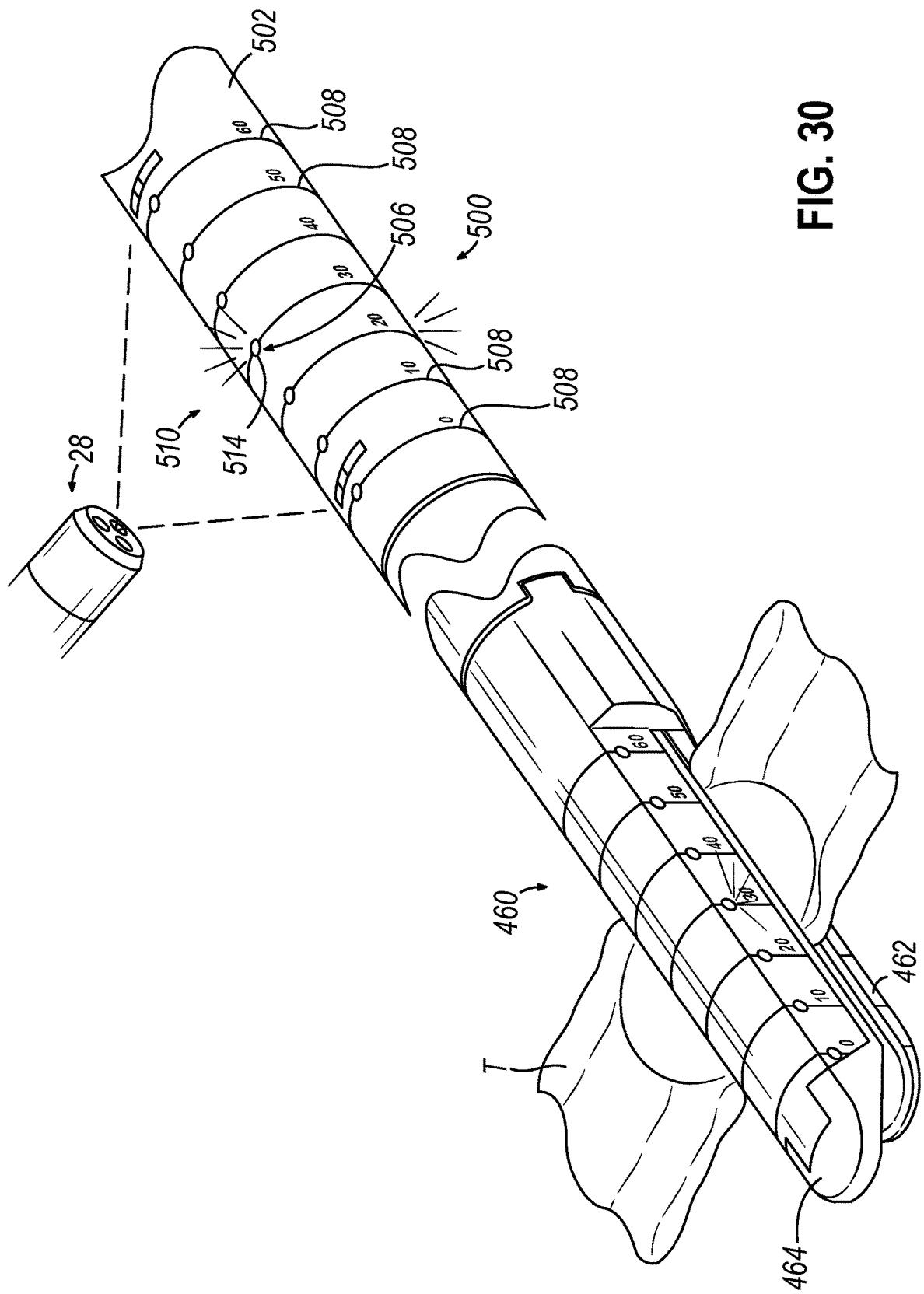
FIG. 30 depicts a perspective view of the elongate shaft of FIG. 28 coupled with a ninth exemplary end effector, shown with the end effector clamping a tissue with a portion of the ninth configuration of illumination features illuminated.

FIGS. 28-30 show an exemplary shaft assembly (500) having an illumination assembly (510). As shown in FIG. 30, shaft assembly (500) is coupled to end effector (460) described above. However, shaft assembly (500) may be coupled to any suitable end effector (116, 210, 300, 330, 360) as would be apparent to one skilled in the art in view of the teachings herein. As illustrated with the broken lines shown in FIG. 30, illumination assembly (510) may be located on any suitable portion of shaft assembly (500) as would be apparent to one skilled in the art in view of the teachings herein.

Shaft assembly (500) includes a static body in the form of a stationary portion (502), and an actuating body in the form of a translating shuttle (504) housed within stationary portion (502). Stationary portion (502) and translating shuttle (504) may be substantially similar to stationary portion (402, 422) and translating shuttle (404, 424) described above, with differences elaborated below. Therefore, translating shuttle (504) is configured to actuate within stationary portion (502) to thereby actuate any suitable firing mechanism(s), (e.g., wedge sled (472)). Therefore, the longitudinal position of translating shuttle (504) relative to stationary portion (502) may correspond to the progression at which any suitable end effector is firing to staple and sever tissue in accordance with the description herein.

Stationary portion (502) defines a linear array of openings (506). Each opening (506) is dimensioned to house a respective light (514) of the illumination assembly (510). Therefore, when the respective light (514) is illuminated in accordance with the description herein, such an illumination will be viewable through openings (506). As best seen in FIG. 30, stationary portion (502) also includes a plurality of indicator markers (508) associated with a respective light (514) of illumination assembly (510). Indicator markers (508) may be substantially similar to indicator markers (305, 335, 451) described above, with difference elaborated below. Rather than being located on an end effector, indicator makers (508) in the current example are located on shaft assembly (500).

Illumination assembly (510) includes at least one contact body in the form of a projection (512) attached to translation shuttle (504) and a linearly array of lights (514) fixed to stationary portion (502) and disposed within a respective opening (506). Each light (514) includes a switch (516). Lights (514) are electrically coupled to each other with a flex circuit (518). Flex circuit (518) extends proximally and couples with a power source configured to power illumination assembly (510) in accordance with the description herein. During the firing process of end effector (460) in order to staple and sever tissue (T) in accordance with the description herein, projection (512) is configured to acuate past switches (516) in a sequential fashion during the firing process of end effector (460). Projection (512) is dimensioned in order to suitably engage switches (516) such that switches (516) in turn activate the illumination of their respective light (514).

Indicator markers (508) are located along discrete longitudinal locations of stationary portion (502) and include a specific value associated with each marker (i.e., the 50 mm marker, the 40 mm marker, the 30 mm marker, etc.). The specific number associated with each marker (508) represents the distance that wedge sled (472) and/or the associated knife member needs to travel further in order to complete the firing processes.

Lights (514) may be located at a corresponding indicator marker (508), while projection (512) is located at a suitable longitudinal location on shuttle (504), such that illumination of an individual light (514) via contact between projection (512) and the corresponding switch (516) may signify the progress at which wedge sled (472) is advanced through lower jaw (462) during the firing process. For example, when projection (512) engages the switch (516) of light (514) that is adjacent to the 20 mm indicator marker (508), that light (514) may illuminate to signify wedge sled (472) still needs to travel 20 mm distally in order to complete the firing processes. As another example, when projection (512) engages the switch (516) of light (514) that is adjacent to the 0 mm indicator marker (508), that light (514) may illuminate to signify wedge sled (472) has reached the distal end of the firing process.

In some instances, once a specific light (514) is illuminated via initial contact with projection (512) actuating distally, that light (514) may stay illuminated until projection (512) engages that specific switch (516) again during proximal retraction of shuttle (504). Therefore, in some instances, the linear array of lights (514) may remain activated to visually approximate the length at which wedge sled has traveled during distal actuation of shuttle (504); while the linear array of lights (514) may be used to visually approximate the length at which shuttle (504) needs to proximally acuate to reach the pre-fired position after the firing process. In some instances, only one light (514) may be activated at a time, such that once the second light (514) activates during distal advancement of shuttle (504), the first light (514) deactivates, and so on. Therefore, in some instances, the linear array of lights (514) may be sequentially activated to visually approximate the general position at which wedge sled is located during the firing process.

Figure 31:
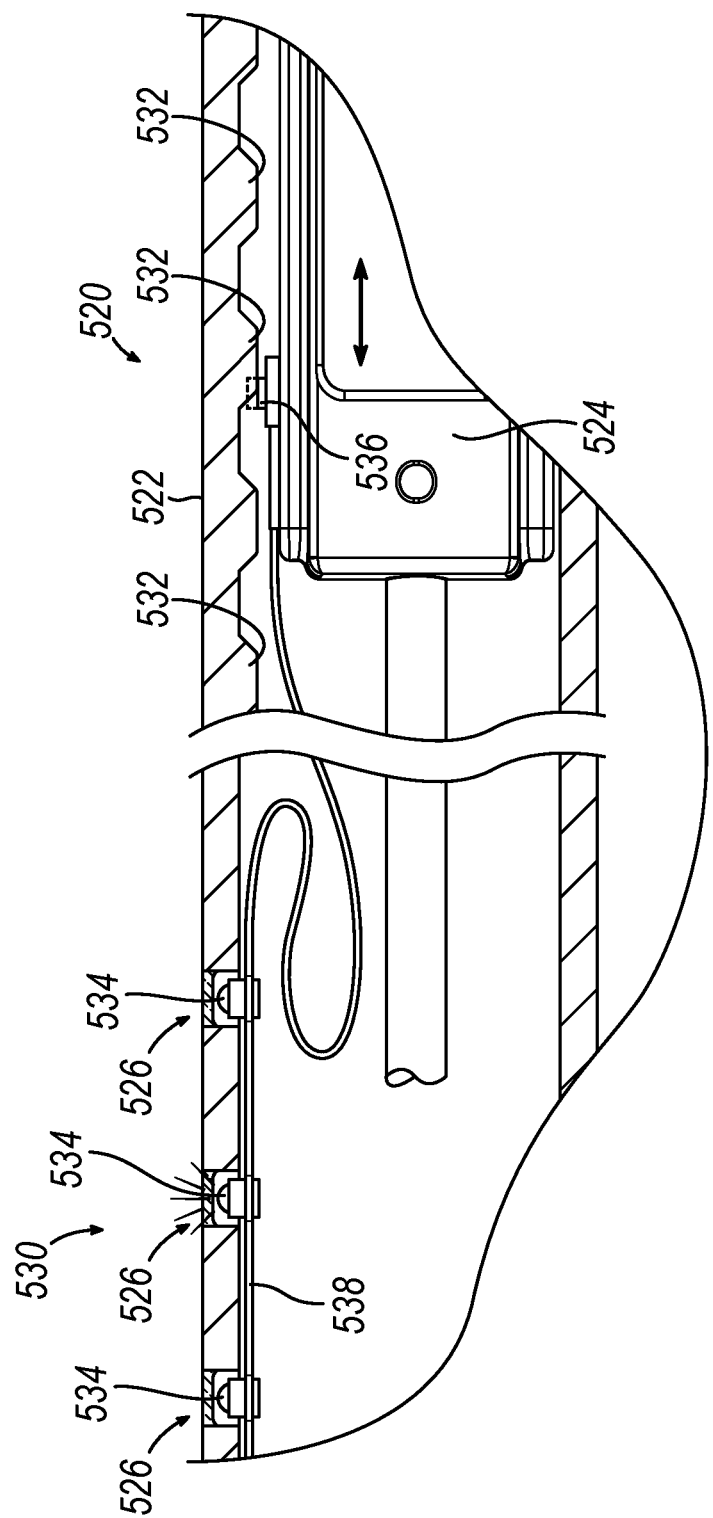
FIG. 31 depicts a side cross-sectional view of a portion of the elongate shaft and end effector of FIG. 30, shown with a portion of the ninth configuration of illumination features illuminated.

FIG. 31 shows another exemplary shaft assembly (520) having an illumination assembly (530). Shaft assembly (520) may be substantially similar to shaft assembly (500) described above, with difference elaborated below. In particular, illumination assembly (530) includes a single switch (536) fixed to a translating shuttle (524), while a stationary portion (522) includes at least one contact body in the form of a longitudinal array of projections (532) configured to selectively engage switch (536) as shuttle (524) actuates during the firing process to thereby activate lights (534) in accordance with the description herein.

Shaft assembly (520) includes a stationary portion (522) and a translating shuttle (524) housed within stationary portion (522). Stationary portion (522) and translating shuttle (524) may be substantially similar to stationary portion (502) and translating shuttle (504) described above, with differences elaborated below. Therefore, translating shuttle (524) is configured to actuate within stationary portion (522) to thereby actuate any suitable firing mechanism(s), (e.g., wedge sled (472)). Therefore, the longitudinal position of translating shuttle (504) relative to stationary portion (502) may correspond to the progression at which any suitable end effector is firing to staple and sever tissue in accordance with the description herein.

Stationary portion (522) defines a linear array of openings (526). Each opening (526) is dimensioned to house a respective light (534) of the illumination assembly (530). Therefore, when the respective light (534) is illuminated in accordance with the description herein, such an illumination will be viewable through openings (526). Stationary portion (522) may include a plurality of indication markers (not shown) similar to indication markers (508) described above.

As mentioned above, illumination assembly (530) includes a linear array of projections (532) fixed to stationary portion (502), a switch (536) attached to shuttle (524), a linear array of lights (534) fixed to stationary portion (522) and disposed within a respective opening (526), and a flex circuit (538). Flex circuit (538) electrical couples linear array of lights (534) with switch (536). Flex circuit (538) extends proximally and couples with a power source configured to power illumination assembly (530) in accordance with the description herein. Switch (536) is configured to activate linear array of lights (534) sequentially, from the proximal most light (534) to the distal most light (534), in response to activating switch (536) repeated number of times. For instance, if switch (536) is activated one time, the proximal most light (534) may illuminate. If switch (536) is then activated a second time, the next proximal most light (534) may illuminate, and so on until the distal most light (534) is illuminated.

During the firing process of end effector (460) in order to staple and sever tissue (T) in accordance with the description herein, switch (536) is configured to acuate past projections (532) in a sequential fashion during the firing process of end effector (460). Projections (532) are dimensioned in order to suitably engage switch (536) such that switch (536) in turn activates to illuminate the linear array of lights (514) in accordance with the description herein. Flex circuit (538) has a suitable length between the proximal most light (535) and switch (536) in order to accommodate translation of shuttle (524) relative to stationary portion (522) during the exemplary firing process. Therefore, switch (536) may actuate relative to lights (534) during the firing process, while flex circuit (538) may suitably maintain the electrical coupling between lights (534) and switch (536).

Similar to lights (514) described above, lights (534) may be located at a corresponding indicator marker (not shown), while the placement of projections (532) and switch (536) are located at a suitable longitudinal location on stationary portion (522) and shuttle (504), respectively, such that illumination of an individual light (534) via contact between the corresponding projection (532) and switch (536) may signify the progress at which wedge sled (472) is advanced through lower jaw (462) during the firing process.

In some instances, once a specific light (534) is illuminated via initial contact between the corresponding projection (532) and switch (536), that light (534) may stay illuminated until the corresponding projection (532) engages switch (536) again during proximal retraction of shuttle (524). Therefore, in some instances, the linear array of lights (534) may remain activated to visually approximate the length at which wedge sled has traveled during distal actuation of shuttle (524); while the linear array of lights (534) may be used to visually approximate the length at which shuttle (524) needs to proximally acuate to reach the pre-fired position after the firing process. In some instances, only one light (534) may be activated at a time, such that once the second light (534) activates during distal advancement of shuttle (524), the first light (534) deactivates, and so on. Therefore, in some instances, the linear array of lights (534) may be sequentially activated to visually approximate the general position at which wedge sled is located during the firing process.

Figure 32:
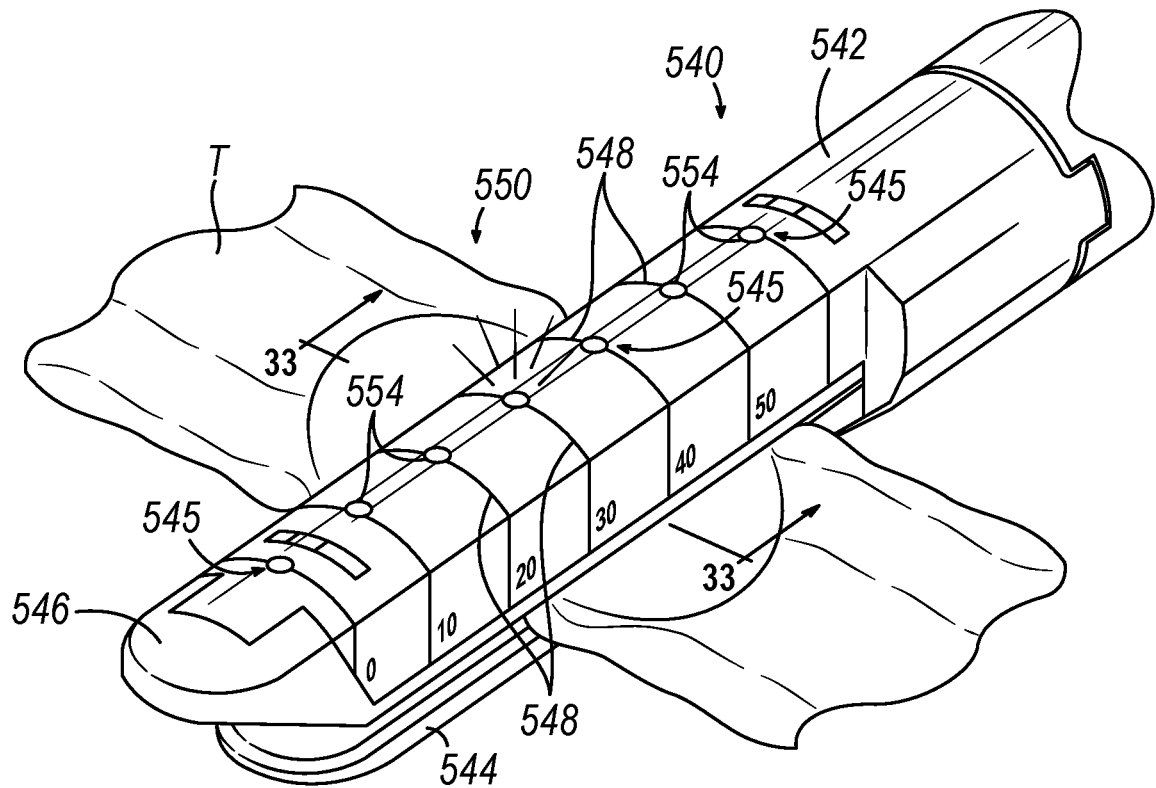
FIG. 32 depicts a perspective view of an tenth exemplary end effector, shown clamping a tissue and having a portion of a tenth configuration of illumination features illuminated.
Figure 33:
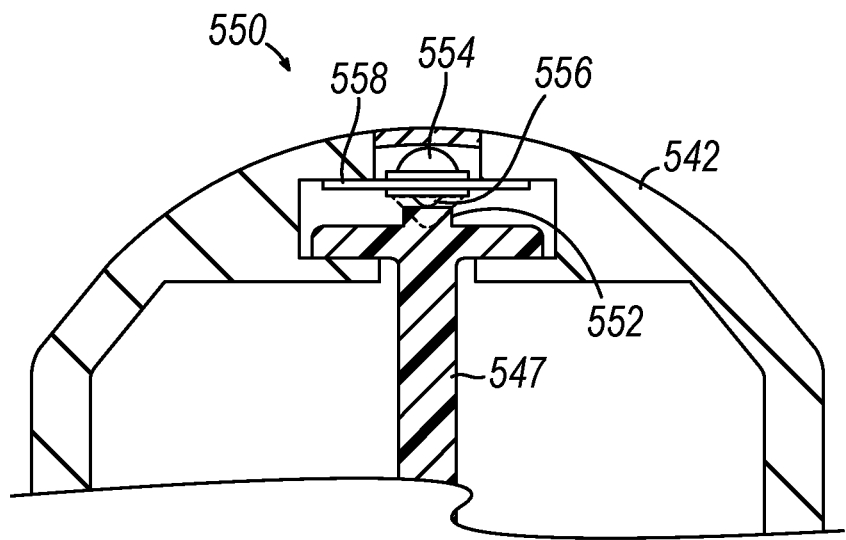
FIG. 33 depicts an end cross-sectional view of a portion of the end effector of FIG. 32.

FIGS. 32-33 show another exemplary end effector (540) that may be readily incorporated into instrument (110) described above. End effector (540) includes a lower jaw (542), an upper jaw (544), a removable staple cartridge (546), and a pusher member (547); which may be substantially similar to lower jaw (152, 212), upper jaw (150, 214), staple cartridge (154, 218), and pusher member/block (166, 236), respectively, with difference elaborated herein. In particular, end effector (540) includes an illumination assembly (550) configured to illuminate to thereby visually represent the progression of a wedge sled actuating through jaws (542, 544) of end effector (540).

Lower jaw (544) includes a plurality of indicator markers (548) that are substantially similar to indicator markers (305, 335, 451) described above. Additionally, lower jaw (544) defines a longitudinal array of openings (545) associated with a corresponding indicator marker (548). Each opening (545) is dimensioned to house a respective light (554) of the illumination assembly (550). Therefore, when the respective light (554) is illuminated in accordance with the description herein, such an illumination will be viewable through openings (545).

Illumination assembly (550) includes a projection (552) attached pusher member (547) and a linearly array of lights (554) fixed to lower jaw (542) and disposed within a respective opening (545). Each light (554) includes a switch (556). Lights (554) are electrically coupled to each other with a flex circuit (558). Flex circuit (558) extends proximally and couples with a power source configured to power illumination assembly (550) in accordance with the description herein. During the firing process of end effector (540) in order to staple and sever tissue (T) in accordance with the description herein, projection (552) is configured to acuate past switches (556) in a sequential fashion during the firing process of end effector (540). Projection (552) is dimensioned in order to suitably engage switches (556) such that switches (556) in turn activate the illumination of their respective light (554).

Indicator markers (548) are located along discrete longitudinal locations of lower jaw (542) and include a specific value associated with each marker (i.e., the 50 mm marker, the 40 mm marker, the 30 mm marker, etc.). The specific number associated with each marker (548) represents the distance that wedge sled and/or the associated knife member needs to travel further in order to complete the firing processes.

Lights (554) may be located at a corresponding indicator marker (548), while projection (552) is located at a suitable longitudinal location on pusher member (547), such that illumination of an individual light (554) via contact between projection (552) and the corresponding switch (556) may signify the progress at which wedge sled is advanced through lower jaw (542) during the firing process. For example, when projection (552) engages the switch (556) of light (554) that is adjacent to the 20 mm indicator marker (548), that light (554) may illuminate to signify wedge sled still needs to travel 20 mm distally in order to complete the firing processes. As another example, when projection (552) engages the switch (556) of light (554) that is adjacent to the 0 mm indicator marker (548), that light (554) may illuminate to signify wedge sled has reached the distal end of the firing process.

Lights (554) may be configured to activate and deactivate illumination using any suitable process as would be apparent to one skilled in the art in view of the teachings herein. For example, lights (554) may activate only when projection (552) is in contact with switch (556). As another example, lights (554) may remain activated after contact with switch (556) until the distal firing process in complete.

Figure 34:
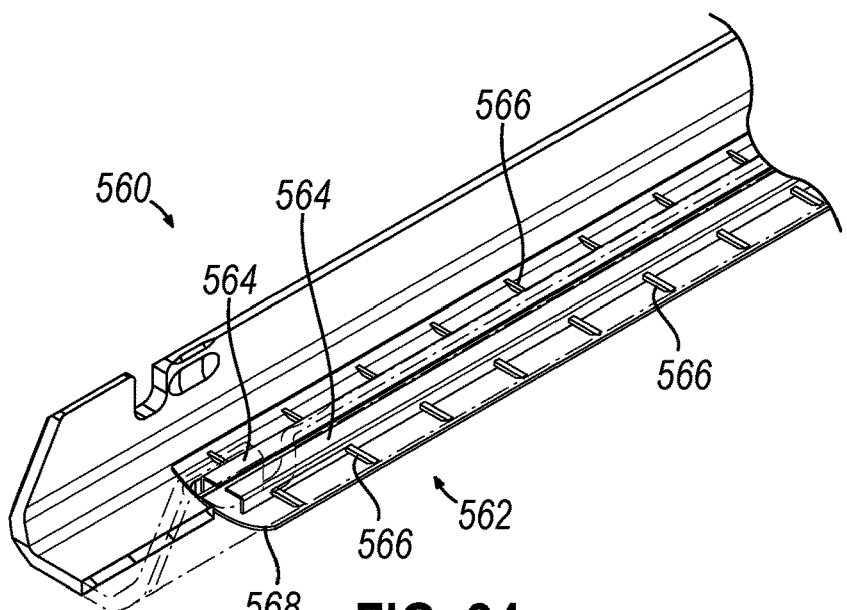
FIG. 34 depicts a perspective view of a lower jaw of an eleventh exemplary end effector, with select portions of the eleventh exemplary end effector omitted or transparent to reveal internal features, the lower jaw having an eleventh configuration of illumination features.
Figure 35:
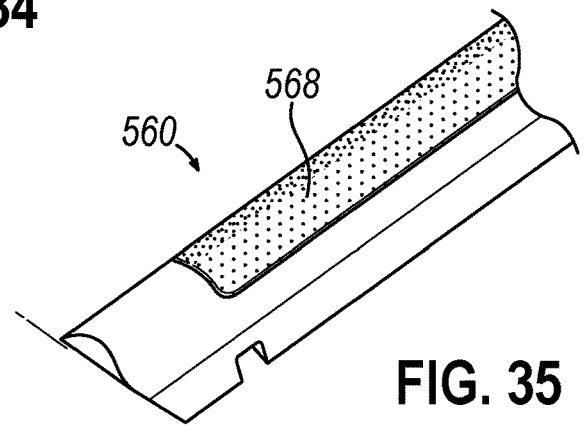
FIG. 35 depicts a bottom perspective view of the end effector of FIG. 34.
Figure 36:
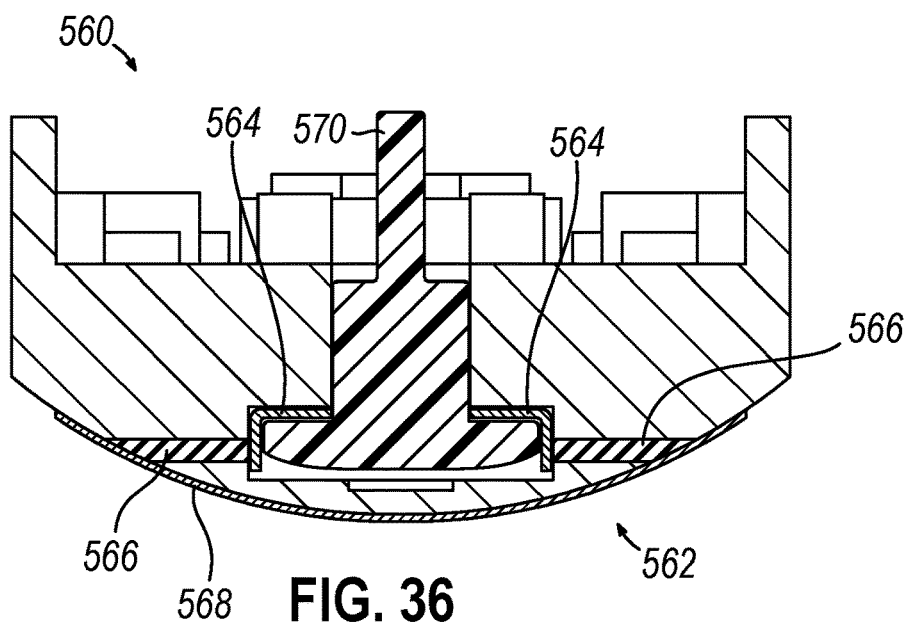
FIG. 36 depicts an end cross-sectional view of the end effector of FIG. 34.

FIGS. 34-36 show an exemplary fire progress monitoring assembly (562) that may visually approximate the firing process via thermochromic film (568), rather than through illumination. In the current example, fire progress monitoring assembly (562) is applied to a lower jaw (560). However, it should be understood that fire progress monitoring assembly (562) may be applied to an upper jaw or any other suitable component as would be apparent to one skilled in the art in view of the teachings herein.

Fire progress monitoring assembly (562) includes a pair of longitudinally extending flex circuits (564) that are electrically separated from each other, a piece of thermochromic film (568) extending along the length of an exterior surface of lower jaw (560), and a plurality of conducting elements (566) extending in two longitudinal arrays, one from each piece of flex circuit (564) to thermochromic film (568). Each flex circuit (564) extends proximally to a power source. However, since flex circuits (564) are electrically separated from each other, the potential circuit formed by power source and both flex circuits (564) may remain normally open. As best seen in FIG. 36, a pusher member (570) is configured to actuate along the length of lower jaw (560) such that a portion of pusher member (570) directly adjacent to each flex circuit (564) is in contact with each flex circuit (564). Pusher member (570) may be formed of a material that is configured to complete an electrical circuit between each flex circuit (564).

Figure 37:
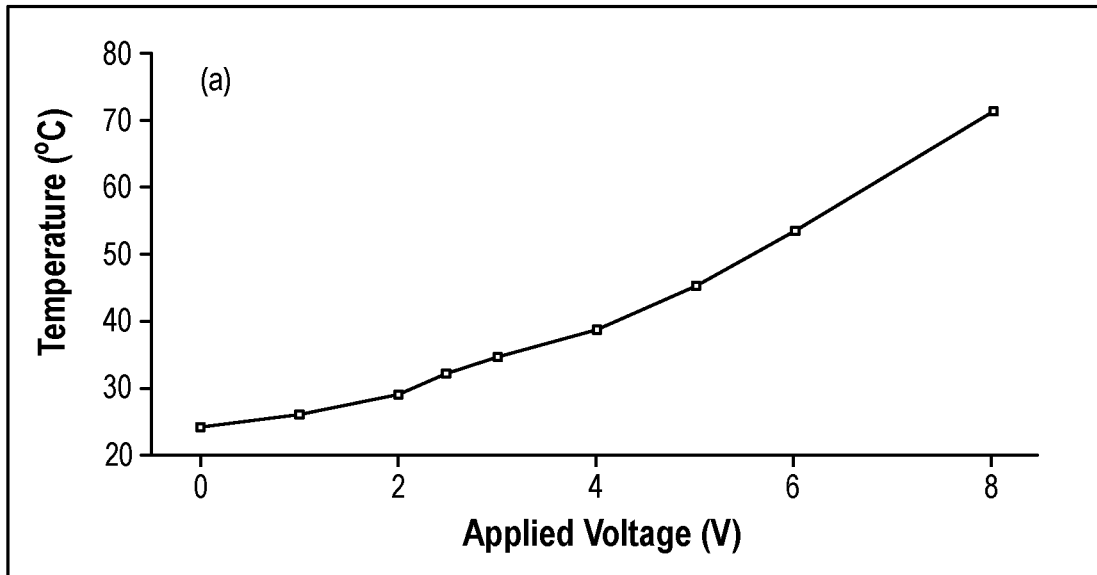
FIG. 37 depicts a first graphical representation of the thermochromic output of the illumination features of the end effector of FIG. 34 during a firing stroke, the first graphical representation illustrating the relationship between applied voltage and temperature.
Figure 38:
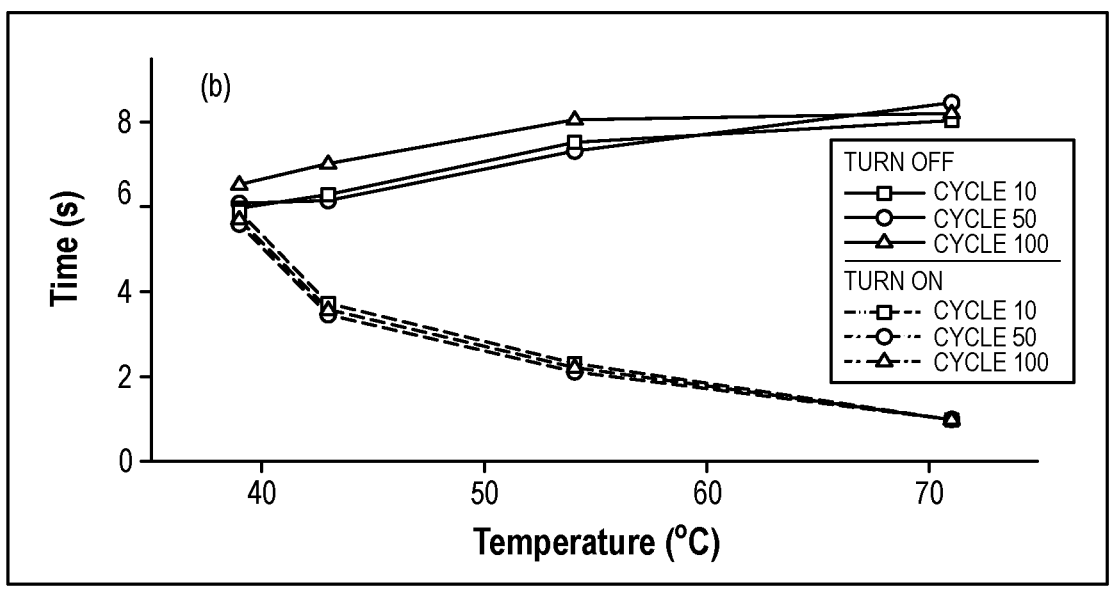
FIG. 38 depicts a second graphical representation of the thermochromic output of the illumination features of the end effector of FIG. 34 during a firing stroke, the second graphical representation illustrating the relationship between temperature and time.

Thermochromic film (568), flex circuits (564) and the array of conducting elements (566) extend along a length of lower jaw (560) corresponding with the travel length required for pusher member (570) to suitably fire an end effector in accordance with the description herein. Thermochromic film (568) is configured to change color in response to a temperature change. As shown in FIGS. 37 and 38, such a temperature change may be function of an applied voltage to thermochromic film (568) over a period a time.

As pusher member (570) actuates along the length of lower jaw (560) in order to fire an end effector in accordance with the description herein, the portion of flex circuits (564) in contact with pusher member (570) may transmit a voltage to thermochromic film (568) via plurality of conducting elements (566). The electrical conducting element (566) closest the pusher member (570) may apply the highest voltage to thermochromic film (568), thereby causing the greater change in color. Therefore, a user may be able to approximate the location of pusher member (570), and therefore approximate the progress of firing an end effector to staple and sever tissue, by viewing where the change in color is located along the length of thermochromic film (568).

While in the current example thermochromic film (568) is used, any other suitable material may be used to provide visual indication of where pusher member (570) is located based on completing an electrical circuit with flex circuits and pusher member (570). For instance, a pressure sensitive material may be incorporated that may show the current flowing the conducting elements (566), thereby providing a visual approximation of the location of pusher member (570).

Figure 39:
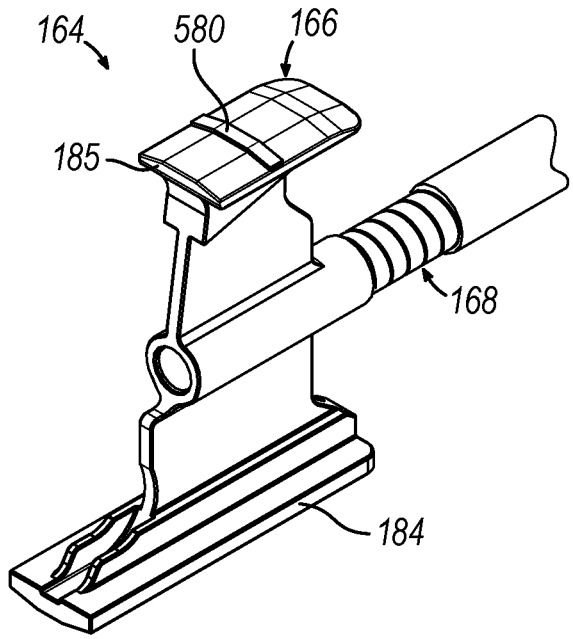
FIG. 39 depicts a second exemplary driving assembly, the driving assembly having a twelfth configuration of illumination features.

In some instances, as shown in FIG. 39, pusher member (166) may incorporate a magnetic strip (580), while a portion of lower jaw (152) or upper jaw (150) that is viewable from an exterior of end effector (116) may include a piece magnetic viewing film extending along a length that pusher member (166) travels in order to fire end effector (116) in accordance with the description herein. Therefore, as pusher member (166) travels along jaws (152, 150), the magnetic viewing film will distort where magnetic strip (580) is located. Such a distortion may provide an approximation of where pusher member (166) is located to track the progression of firing end effector (116).

Figure 40:
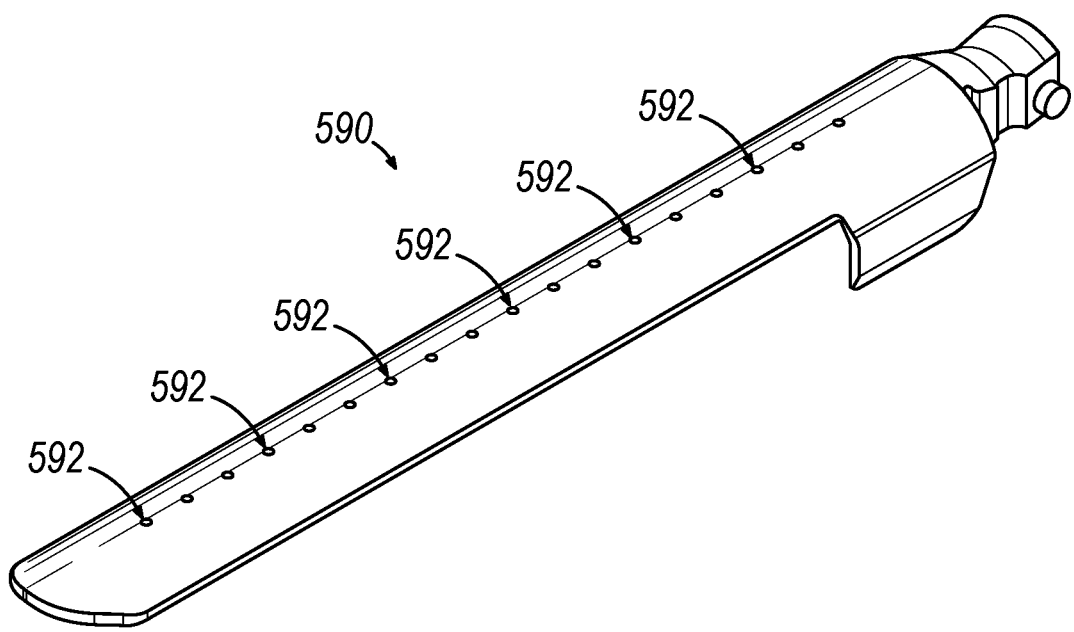
FIG. 40 depicts a pivotable anvil configured for use with the driving assembly of FIG. 39.

FIG. 40 show an exemplary upper jaw (590) that may be used to track the progression of pusher member (166) traveling along the length of end effector (116) in order to staple and sever tissue in accordance with the description herein. Therefore, upper jaw (590) may be readily incorporated into end effector (116) in replacement of upper jaw (150) described above.

Upper jaw (590) includes a plurality of micro-holes (592) extending along a length of upper jaw (590). Micro-holes (592) extend from an interior channel of upper jaw (590) dimensioned to receive slidably pusher number (166) all the way to an exterior surface of upper jaw (590). The interior channel of upper jaw (590) maybe "flooded" with light via an LED light or any other suitable light source as would be apparent to one skilled in the art in view of the teachings herein. Therefore, light emitted from the light source within the interior channel of upper jaw (590) may illuminate out of all micro-holes (592). As pusher member (166) acerates within the interior channel of upper jaw (590), the portion of pusher member (166) directly adjacent to specific micro-holes (592) may block light from illuminating out of directly adjacent micro-holes (592). Therefore, a user may be able to approximate the location of pusher member (166) during the exemplary firing of end effector (116) by noting which micro-holes (592) are not illuminating light.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a shaft assembly; (b) an end effector extending distally from the shaft assembly, wherein the end effector comprises: (i) an upper jaw, (ii) a lower jaw, wherein the upper jaw and the lower jaw are configured to actuate relative to each other between an open position and a closed position, (iii) a stapling assembly supported by the lower jaw, wherein the stapling assembly comprises a plurality of staples, and (iv) a drive member configured to actuate within and relative to at least one of the upper jaw or the lower jaw in the closed position to fire the plurality of staples out of the stapling assembly; and (c) a drive member visualization assembly configured to provide an electronic indication linked to a physical location of the drive member within the end effector as the drive member advances longitudinally through the end effector.

Example 2

The apparatus of any one or more or the preceding Examples, wherein the drive member comprises a knife, wherein a portion of the drive member visualization assembly configured to provide the electronic indication is coupled to the knife.

Example 3

The apparatus of any one or more or the preceding Examples, wherein the portion of the drive member visualization assembly comprises a light.

Example 4

The apparatus of any one or more or the preceding Examples, wherein the light is configured to provide the electronic indication via illumination.

Example 5

The apparatus of any one or more or the preceding Examples, further comprising a camera system.

Example 6

The apparatus of any one or more or the preceding Examples, wherein the electronic indication is at least sporadically visible to the camera system.

Example 7

The apparatus of any one or more or the preceding Examples, wherein the camera system further comprises an endoscope.

Example 8

The apparatus of any one or more or the preceding Examples, wherein drive member visualization assembly comprises a detection assembly associated with the shaft assembly, wherein detection assembly is configured to detect actuation of the drive member within the end effector.

Example 9

The apparatus of any one or more or the preceding Examples, wherein the drive member visualization assembly comprises a display assembly associated with the shaft assembly, wherein the display assembly is configured to visualize the detections generated by the detection assembly.

Example 10

The apparatus of any one or more or the preceding Examples, wherein the drive member visualization assembly comprises a longitudinal array of lights.

Example 11

The apparatus of any one or more or the preceding Examples, wherein the longitudinal array of lights is fixed to the end effector.

Example 12

The apparatus of any one or more or the preceding Examples, wherein the longitudinal array of lights is fixed to the shaft assembly.

Example 13

The apparatus of any one or more or the preceding Examples, wherein the apparatus comprises a surgical site visualization assembly.

Example 14

The apparatus of any one or more or the preceding Examples, wherein the surgical site visualization assembly is configured to provide an augmented display of the electronic indication.

Example 15

The apparatus of any one or more or the preceding Examples, wherein the drive member visualization assembly comprises a Linear Variable Displacement Transformer.

Example 16

An apparatus comprising: (a) a shaft assembly; (b) an end effector extending distally from the shaft assembly, wherein the end effector comprises: (i) a stapling jaw, (ii) an anvil jaw, wherein the anvil jaw and the stapling jaw are configured to actuate relative to each other between an open position and a closed position, (iii) a stapling assembly associated with the stapling jaw, wherein the stapling assembly comprises a plurality of staples, and (iv) a drive member configured to actuate along a firing stroke relative to the stapling jaw and the anvil jaw in the closed position to fire the plurality of staples out of the stapling assembly; and (c) a drive member visualization assembly configured to approximate a location of the drive member within end effector as the drive member actuates along the firing stroke.

Example 17

The apparatus of any one or more or the preceding Examples, wherein the drive member visualization assembly comprises an array of lights associated with the stapling assembly.

Example 18

The apparatus of any one or more or the preceding Examples, wherein the drive member visualization assembly comprises a linear array of indicators associated with the stapling jaw.

Example 19

An apparatus comprising: (a) a shaft assembly; (b) an end effector extending distally from the shaft assembly, wherein the end effector comprises: (i) an upper jaw, (ii) a lower jaw, wherein the upper jaw and the lower jaw are configured to actuate relative to each other between an open position and a closed position, and (iii) a drive member comprising a knife configured to actuate relative to the upper jaw and the lower jaw in the closed position; and (c) a drive member approximation assembly configured to detect the drive member reaching each of a plurality of discrete locations within the end effector, wherein the drive member approximation assembly is configured to provide a visual indication indicative of a location of the drive member relative to the plurality of discrete locations.

Example 20

The apparatus of any one or more or the preceding Examples, further comprising a replaceable staple cartridge configured to selectively couple with the lower jaw, wherein the replaceable staple cartridge comprises a plurality of staples, wherein the drive member is configured to actuate relative to the upper jaw and the lower jaw in the closed position to fire the plurality of staples out of the replaceable staple cartridge against the upper jaw.

IV. Miscellaneous

Any one or more of the teachings, expressions, embodiments, examples, etc. described herein may be combined with any one or more of the teachings, expressions, embodiments, examples, etc. described in U.S. patent application Ser. No. 17/402,674, entitled "Methods of Operating a Robotic Surgical Stapler," filed on Aug. 16, 2021, published as U.S. Pub. No. 2023/0051361 on Feb. 16, 2023; U.S. patent application Ser. No. 17/402,675, entitled "Multi-Threshold Motor Control Algorithm for Powered Surgical Stapler," filed on Aug. 16, 2021, issued as U.S. Pat. No. 11,992,209 on May 28, 2024; U.S. patent application Ser. No. 17/402,677, entitled "Variable Response Motor Control Algorithm for Powered Surgical Stapler," filed on Aug. 16, 2021, issued as U.S. Pat. No. 11,944,297 on Apr. 2, 2024;

U.S. patent application Ser. No. 17/402,679, entitled "Powered Surgical Stapler Having Independently Operable Closure and Firing Systems," filed on Aug. 16, 2021, issued as U.S. Pat. No. 11,779,332 on Oct. 10, 2023; U.S. patent application Ser. No. 17/402,695, entitled "Firing System Features for Surgical Stapler," filed on Aug. 16, 2021, published as U.S. Pub. No. 2023/0050707 on Feb. 16, 2023; U.S. patent application Ser. No. 17/402,701, entitled "Multiple-Sensor Firing Lockout Mechanism for Powered Surgical Stapler," filed on Aug. 16, 2021, issued as U.S. Pat. No. 11,992,210 on May 28, 2024; U.S. patent application Ser. No. 17/402,703, entitled "Proximally Located Firing Lockout Mechanism for Surgical Stapler," filed on Aug. 16, 2021, issued as U.S. Pat. No. 11,957,336 on Apr. 16, 2024; U.S. patent application Ser. No. 17/402,720, entitled "Cartridge-Based Firing Lockout Mechanism for Surgical Stapler," filed on Aug. 16, 2021, issued as U.S. Pat. No. 12,011,164 on Jun. 18, 2024; U.S. patent application Ser. No. 17/402,732, entitled "Sled Restraining Member for Surgical Stapler," filed on Aug. 16, 2021, issued as U.S. Pat. No. 11,986,182 on May 21, 2024; U.S. patent application Ser. No. 17/402,744, entitled "Adjustable Power Transmission Mechanism for Powered Surgical Stapler," filed on Aug. 16, 2021, issued as U.S. Pat. No. 12,029,508 on Jul. 9, 2024; U.S. patent application Ser. No. 17/402,749, entitled "Firing Bailout System for Powered Surgical Stapler," filed on Aug. 16, 2021, issued as U.S. Pat. No. 12,089,842 on Sep. 17, 2024; and/or U.S. patent application Ser. No. 17/402,759, entitled "Deflectable Firing Member for Surgical Stapler," filed on Aug. 16, 2021, published as U.S. Pub. No. 2023/0052307 on Feb. 16, 2023. The disclosure of each of these applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a shaft;
   (b) an end effector extending distally from the shaft, wherein the end effector comprises:
      (i) an upper jaw,
      (ii) a lower jaw, wherein the upper jaw and the lower jaw are configured to actuate relative to each other between an open position and a closed position,
      (iii) a staple cartridge supported by the lower jaw, wherein the staple cartridge comprises a cartridge body and a plurality of staples, wherein the cartridge body houses the plurality of staples, and
      (iv) a driver configured to actuate within and relative to at least one of the upper jaw or the lower jaw in the closed position to fire the plurality of staples out of the cartridge body, wherein the driver comprises:
         (A) a wedge sled slidably contained within the cartridge body of the staple cartridge, and
         (B) a pusher slidably coupled with the shaft, wherein the pusher is configured to distally actuate the wedge sled to fire the staples from the staple cartridge; and
   (c) a driver visualization assembly configured to provide an electronic indication linked to a physical location of the driver within the end effector as the driver advances longitudinally through the end effector, wherein the driver visualization assembly comprises:
      (i) a light attached to the wedge sled, and
      (ii) a flex circuit associated with the lower jaw, wherein the flex circuit is configured to activate the light as the wedge sled distally actuates in order to fire the plurality of staples out of the staple cartridge.

2. The apparatus of claim 1, wherein the driver comprises a knife, wherein the light of the driver visualization assembly configured to provide the electronic indication is coupled to the knife.

3. The apparatus of claim 1, wherein the light is configured to provide the electronic indication via illumination.

4. The apparatus of claim 1, further comprising a camera system.

5. The apparatus of claim 4, wherein the electronic indication is at least sporadically visible to the camera system.

6. The apparatus of claim 4, wherein the camera system further comprises an endoscope.

7. The apparatus of claim 1, wherein the driver comprises a knife associated with the pusher.

8. The apparatus of claim 1, wherein the flex circuit is configured to wirelessly power the light.

9. An apparatus comprising:
(a) a shaft assembly;
(b) an end effector extending distally from the shaft assembly, wherein the end effector comprises:
(i) a stapling jaw,
(ii) an anvil jaw, wherein the anvil jaw and the stapling jaw are configured to actuate relative to each other between an open position and a closed position,
(iii) a removable stapling cartridge associated with the stapling jaw, wherein the removable stapling cartridge comprises a cartridge body and a plurality of staples housed within the cartridge body, and
(iv) a driver configured to actuate along a firing stroke relative to the stapling jaw and the anvil jaw in the closed position to fire the plurality of staples out of the cartridge body, wherein the driver comprises:
(A) a wedge sled slidably contained within the cartridge body, and
(B) a pusher configured to drive the wedge sled distally within the cartridge body to fire the plurality of staples out of the cartridge body; and
(c) a driver visualization assembly configured to approximate a location of the driver within the end effector as the driver actuates along the firing stroke, wherein the driver visualization assembly comprises:
(i) an array of lights extending along a length of the end effector, and
(ii) a contact attached to the wedge sled, wherein the contact is configured to sequentially activate the array of lights as the wedge sled is driven distally within the cartridge body.

10. The apparatus of claim 9, wherein the wedge sled further comprises an identifying resistor in electrical communication with the contact.

11. The apparatus of claim 9, wherein the array of lights are associated with the stapling jaw.

12. An apparatus comprising:
(a) a shaft assembly comprising a static body and an actuating body configured to translate relative to the static body;
(b) an end effector extending distally from the shaft assembly, wherein the end effector comprises:
(i) an upper jaw,
(ii) a lower jaw, wherein the upper jaw and the lower jaw are configured to actuate relative to each other between an open position and a closed position, and
(iii) a driver comprising a knife configured to actuate relative to the upper jaw and the lower jaw in the closed position, wherein the actuating body of the shaft is configured to actuate the driver; and
(c) a driver approximation assembly configured to detect the driver reaching each of a plurality of discrete locations within the end effector, wherein the driver approximation assembly is configured to provide a visual indication indicative of a location of the driver relative to the plurality of discrete locations, wherein the driver approximation assembly comprises:
(A) a linear array of lights,
(B) at least one switch associated with either the static body or the actuating body,
(C) at least one contact body, wherein the at least one switch and the at least one contact body are configured to interact with each other in response to the actuating body translating relative to the static body.

13. The apparatus of claim 12, further comprising a replaceable staple cartridge configured to selectively couple with the lower jaw, wherein the replaceable staple cartridge comprises a plurality of staples, wherein the driver is configured to actuate relative to the upper jaw and the lower jaw in the closed position to fire the plurality of staples out of the replaceable staple cartridge against the upper jaw.

14. The apparatus of claim 13, wherein the array of lights is fixed to the replaceable staple cartridge.

15. The apparatus of claim 14, wherein the replacement staple cartridge comprises an electrical chip.

16. The apparatus of claim 12, wherein the array of lights is fixed to the lower jaw.

17. The apparatus of claim 12, wherein the driver approximation assembly comprises a flex circuit in communication with the array of lights.

* * * * *